(12) United States Patent
Rubin et al.

(10) Patent No.: US 7,981,609 B2
(45) Date of Patent: Jul. 19, 2011

(54) METHODS FOR IDENTIFYING AND USING SNP PANELS

(75) Inventors: Mark A. Rubin, Cambridge, MA (US); Francesca Demichelis, Cambridge, MA (US); Levi A. Garraway, Newton, MA (US); William R. Sellers, Brookline, MA (US)

(73) Assignees: The Brigham and Women's Hospital, Inc., Boston, MA (US); Dana-Farber Cancer Institute, Inc., Boston, MA (US)

( * ) Notice: Subject to any disclaimer, the term of this patent is extended or adjusted under 35 U.S.C. 154(b) by 715 days.

(21) Appl. No.: 11/811,149

(22) Filed: Jun. 8, 2007

(65) Prior Publication Data
US 2009/0004652 A1 Jan. 1, 2009

Related U.S. Application Data

(60) Provisional application No. 60/812,477, filed on Jun. 9, 2006.

(51) Int. Cl.
*C12Q 1/68* (2006.01)
(52) U.S. Cl. .......................................... 435/6
(58) Field of Classification Search ........................ None
See application file for complete search history.

(56) References Cited

U.S. PATENT DOCUMENTS
| | | | |
|---|---|---|---|
| 6,709,816 B1 | 3/2004 | Huang et al. |
| 7,332,277 B2 | 2/2008 | Dhallan |
| 7,361,468 B2 | 4/2008 | Liu et al. |

FOREIGN PATENT DOCUMENTS
WO 2007/146819 12/2007

OTHER PUBLICATIONS

Vallone, P.M. et al. Forensic Science International 149:279-286 (published online Sep. 23, 2004).*
Beroukhim, R., "Inferring Loss-of-Heterozygosity from Unpaired Tumors Using High-Density Oligonucleotide SNP Arrays," *PLOS Computational Biology*, 2(5):0323-0332 (2006).
Helisalmi, et al., "Lack of Genetic Association Between PPARG Gene Polymorphisms and Finnish late-Onset Alzheimer's Disease," *Neuroscience Letters*, 441:233-236, (2008).
Ikediobi, O.N., "Mutation Analysis of 24 Known Cancer Genes in the NCI-60 Cell Line Set," *Mol. Cancer Ther.*, 5(11):2606-2612, (2006).
Lee, "Gene SNPs and Mutations in Clinical Genetic Testing: Haplotype-Based Testing and Analysis," *Mutation Research*, 573:195-204, (2005).
Wright, W., "Genetic Screening of the LPL Gene in Hypertriglyceridaemic Patients," *Atheroscleorsis*, 199:187-192, (2008).
International Search Report and Written Opinion from Application No. PCT/US2007/70782, mailed Aug. 22, 2008.
Bright et al., "Generation and genetic characterization of mmortal human prostate epithelial cell lines derived from primary cancer specimens," *Cancer Res.*, 57:995-1002 (1997).
Demichelis et al., "SNP panel identification assay (SPIA): a genetic-based assay for the identification of cell lines," *Nucleic Acids Research*, 36(7):2446-2456 (2008).
Garraway et al., "Integrative genomic analyses identify MITF as a lineage survival oncogene amplified in malignant melanoma," *Nature*, 436:117-122 (2005).
Gaustadnes et al., "Validation of the use of DNA pools and primer extension in association studies of sporadic colorectal cancer for selection of candidate SNPs," *Hum. Mutat.*, 27:187-194 (2006).
Heaton et al., "Selection and use of SNP markers for animal identification and paternity analysis in U.S. beef cattle," *Mamm. Genome*, 13:272-281 (2002).
Kidd et al., "Developing a SNP panel for forensic identification of individuals," *Forensic Sci. Int.*, 164:20-32 (2006).
Lao et al., "Proportioning whole-genome single-nucleotide-polymorphism diversity for the identification of geographic population structure and genetic ancestry," *Am. J. Hum. Genet.*, 78:680-690 (2006).
Liscovitch et al., "A case study in misidentification of cancer cell lines: MCF-7/AdrR cells (re-designated NCI/ADR-RES) are derived from OVCAR-8 human ovarian carcinoma cells," *Cancer Lett.*, 245:350-352 (2007).
Macoska et al., "Genetic characterization of immortalized human prostate epithelial cell cultures. Evidence for structural rearrangements of chromosome 8 and i(8q) chromosome formation in primary tumor-derived cells," *Cancer Genet. Cytogenet.*, 120:50-57 (2000).
Masters et al., "Short tandem repeat profiling provides an international reference standard for human cell lines," *Proc. Natl. Acad. Sci. USA*, 98:8012-8017 (2001).
Parson et al., "Cancer cell line identification by short tandem repeat profiling: power and limitations," *FASEB J.*, 19:434-436 (2005).
Ross et al., "Systematic variation in gene expression patterns in human cancer cell lines," *Nat. Genet.*, 24:227-235 (2000).
Tang et al., "Chip-based genotyping by mass spectrometry," *Proc. Natl. Acad. Sci. USA*, 96:10016-10020 (1999).
Zhao et al., "Homozygous deletions and chromosome amplifications in human lung carcinomas revealed by single nucleotide polymorphism array analysis," *Cancer Res.*, 65:5561-5570 (2005).

* cited by examiner

*Primary Examiner* — Diana B Johannsen
(74) *Attorney, Agent, or Firm* — Fish & Richardson P.C.

(57) ABSTRACT

Described are methods for identifying single nucleotide polymorphism (SNPs) that are useful for analyzing genetic samples, and for using said SNPs to determine genetic identity of samples.

12 Claims, 25 Drawing Sheets
(5 of 25 Drawing Sheet(s) Filed in Color)

| SNPs | SNP Index | Selection Rate | PercHet Test | dbSNPRSID | Chromo | Cytoband | Associated Gene | Het_Asian | Het_AfAm | Het_Cauc |
|---|---|---|---|---|---|---|---|---|---|---|
| SNP_A-1733450 | 4122 | 0.68 | 0.302 | rs1446331 | 11 | p11.2 | NM_002231 | 0.1913 | 0.3367 | 0.4592 |
| SNP_A-1688152 | 2062 | 0.66 | 0.241 | rs915286 | 13 | q14.11 | NM_020751 | 0.4717 | 0.4929 | 0.4929 |
| SNP_A-1685378 | 1946 | 0.62 | 0.259 | rs950400 | 13 | q21.31 | ENST00000324792 | 0.4989 | 0.3628 | 0.4989 |
| SNP_A-1713458 | 3196 | 0.57 | 0.245 | rs1459543 | 4 | q26 | NM_004784 | 0.4274 | 0.3367 | 0.4955 |
| SNP_A-1703635 | 2770 | 0.55 | 0.314 | rs2040075 | 1 | p21.3 | NM_152369 | 0.4274 | 0.4955 | 0.5 |
| SNP_A-1645946 | 188 | 0.54 | 0.296 | rs721257 | 3 | p26.1 | NM_000844 | 0.1913 | 0.4929 | 0.4974 |
| SNP_A-1732269 | 4063 | 0.54 | 0.321 | rs134846 | 22 | q13.31 | NM_013236 | 0.3977 | 0.4181 | 0.4989 |
| SNP_A-1719177 | 3457 | 0.53 | 0.321 | rs1456572 | 2 | q33.1 | NM_015265 | 0.3367 | 0.3501 | 0.4997 |
| SNP_A-1698987 | 2543 | 0.51 | 0.302 | rs623155 | 6 | q14.1 | X82272 | 0.4362 | 0.4929 | 0.4974 |
| SNP_A-1749895 | 4841 | 0.5 | 0.346 | rs29620 | 5 | q35.1 | NM_003862 | 0.4657 | 0.3501 | 0.5 |
| SNP_A-1746418 | 4702 | 0.49 | 0.385 | rs1520178 | 12 | q24.21 | NM_015335 | 0.4181 | 0.4997 | 0.4955 |
| SNP_A-1755396 | 5048 | 0.47 | 0.245 | rs1943889 | 18 | q22.3 | NM_152676 | 0.477 | 0.4955 | 0.4898 |
| SNP_A-1678628 | 1657 | 0.46 | 0.264 | rs1366686 | 4 | q31.22 | NM_031956 | 0.4989 | 0.2778 | 0.5 |
| SNP_A-1685068 | 1927 | 0.45 | 0.389 | rs717770 | 9 | q34.13 | NM_207417 | 0.4861 | 0.4989 | 0.4955 |
| SNP_A-1689044 | 2105 | 0.45 | 0.278 | rs1157929 | 11 | p14.3 | ENST00000354193 | 0.4181 | 0.3501 | 0.5 |
| SNP_A-1669865 | 1270 | 0.44 | 0.269 | rs2332909 | 14 | q24.2 | NM_004296 | 0.4362 | 0.4974 | 0.4997 |
| SNP_A-1679544 | 1688 | 0.44 | 0.358 | rs978422 | 21 | q21.1 | NM_002772 | 0.2778 | 0.4082 | 0.477 |
| SNP_A-1649266 | 363 | 0.43 | 0.259 | rs1360005 | 10 | q24.1 | NM_015385 | 0.1327 | 0.4181 | 0.4861 |
| SNP_A-1695795 | 2393 | 0.43 | 0.308 | rs2406756 | 4 | q28.3 | NM_014331 | 0.4974 | 0.4181 | 0.4955 |
| SNP_A-1652358 | 492 | 0.41 | 0.346 | rs1605727 | 5 | q23.1 | NM_016644 | 0.4657 | 0.4929 | 0.4717 |
| SNP_A-1700959 | 2648 | 0.41 | 0.396 | rs1888668 | 10 | p13 | NM_020397 | 0.4955 | 0.375 | 0.4819 |
| SNP_A-1689725 | 2134 | 0.4 | 0.321 | rs1957491 | 14 | q21.2 | NM_032135 | 0.477 | 0.4861 | 0.4717 |
| SNP_A-1719073 | 3450 | 0.4 | 0.358 | rs1929715 | 9 | q21.31 | NM_005077 | 0.1913 | 0.4444 | 0.4989 |
| SNP_A-1742235 | 4507 | 0.4 | 0.291 | rs953952 | 5 | q15 | NM_018343 | 0.5 | 0.375 | 0.4997 |
| SNP_A-1748157 | 4756 | 0.4 | 0.385 | rs1341112 | 6 | q16.3 | NM_020771 | 0.4955 | 0.3977 | 0.4997 |

FIG. 10A-1

| SNPs | SNP Index | Selection Rate | PercHet Test | dbSNPRSID | Chromo | Cytoband | Associated Gene | Het_Asian | Het_AfAm | Het_Cauc |
|---|---|---|---|---|---|---|---|---|---|---|
| SNP_A-1750303 | 4862 | 0.4 | 0.314 | rs1916503 | 10 | q21.1 | NM_033056 | 0.4893 | 0.4592 | 0.4929 |
| SNP_A-1677112 | 1581 | 0.39 | 0.364 | rs717615 | 4 | p16.1 | ENST00000264785 | 0.4997 | 0.4444 | 0.4861 |
| SNP_A-1690117 | 2146 | 0.39 | 0.269 | rs950408 | 18 | q21.32 | NM_031891 | 0.4861 | 0.4082 | 0.4955 |
| SNP_A-1703921 | 2780 | 0.39 | 0.415 | rs952111 | 6 | q21 | NM_153612 | 0.4955 | 0.4362 | 0.4717 |
| SNP_A-1747887 | 4748 | 0.39 | 0.302 | rs1594372 | 4 | q13.1 | ENST00000273844 | 0.4974 | 0.4898 | 0.4819 |
| SNP_A-1687664 | 2042 | 0.38 | 0.327 | rs1241906 | 14 | q31.2 | NM_013231 | 0.4819 | 0.3084 | 0.4717 |
| SNP_A-1743509 | 4568 | 0.37 | 0.37 | rs719736 | 2 | q32.1 | NM_138285 | 0.4955 | 0.1723 | 0.4989 |
| SNP_A-1757163 | 5139 | 0.36 | 0.296 | rs952645 | 13 | q33.1 | NM_000452 | 0.4274 | 0.2934 | 0.4997 |
| SNP_A-1660059 | 836 | 0.35 | 0.296 | rs 642218 | 4 | q28.2 | NM_173487 | 0.4274 | 0.4861 | 0.4929 |
| SNP_A-1644474 | 117 | 0.34 | 0.241 | rs1410600 | 10 | q24.1 | AL117472 | 0.1327 | 0.4444 | 0.4861 |
| SNP_A-1700482 | 2625 | 0.34 | 0.345 | rs1934009 | 6 | q16.3 | NM_021956 | 0.3228 | 0.3228 | 0.477 |
| SNP_A-1697629 | 2475 | 0.32 | 0.352 | rs965903 | 9 | q22.32 | NM_138497 | 0.3228 | 0.3628 | 0.4861 |
| SNP_A-1720799 | 3533 | 0.32 | 0.404 | rs1106349 | 12 | q24.23 | NM_194286 | 0.477 | 0.4274 | 0.4989 |

FIG. 10A-2

| SNP | Index SNP | PercHetin Test | Selection Rate | dbSNPSID | Chrom | Cytoband | Associated Gene | Het_Asian | Het_AfAm | Het_Cauc |
|---|---|---|---|---|---|---|---|---|---|---|
| SNP_A-1731519 | 4022 | 0.404 | 0.85 | rs1564935 | 2 | q21.2 | NM_002410 | 0.375 | 0.1913 | 0.477 |
| SNP_A-1754984 | 5039 | 0.491 | 0.83 | rs723725 | 7 | p21.1 | NM_015132 | 0.4082 | 0.2616 | 0.4974 |
| SNP_A-1642657 | 34 | 0.458 | 0.79 | rs1568645 | 7 | p14.1 | M80629 | 0.4592 | 0.4717 | 0.4997 |
| SNP_A-1715815 | 3316 | 0.478 | 0.77 | rs487616 | 1 | q31.1 | NM_199051 | 0.4929 | 0.4819 | 0.4989 |
| SNP_A-1750569 | 4871 | 0.469 | 0.77 | rs967968 | 2 | p15 | NM_014709 | 0.3977 | 0.4929 | 0.4955 |
| SNP_A-1705845 | 2855 | 0.478 | 0.73 | rs967016 | 2 | p11.2 | NM_178839 | 0.2276 | 0.4444 | 0.4929 |
| SNP_A-1651260 | 445 | 0.556 | 0.73 | rs721087 | 2 | p25.2 | NM_003310 | 0.3501 | 0.4974 | 0.5 |
| SNP_A-1644620 | 122 | 0.407 | 0.72 | rs718015 | 7 | p14.1 | NM_130442 | 0.4898 | 0.5 | 0.4997 |
| SNP_A-1702463 | 2730 | 0.44 | 0.72 | rs2254896 | 14 | q11.2 | NM_001001912 | 0.4521 | 0.4929 | 0.4861 |
| SNP_A-1671618 | 1335 | 0.44 | 0.67 | rs722152 | 12 | q22 | NM_005761 | 0.4861 | 0.4997 | 0.4974 |
| SNP_A-1726016 | 3776 | 0.444 | 0.66 | rs2414908 | 15 | q22.31 | NM_207338 | 0.4819 | 0.5 | 0.4472 |
| SNP_A-1745003 | 4627 | 0.392 | 0.64 | rs2868931 | 18 | p11.22 | NM_153000 | 0.4898 | 0.4592 | 0.477 |
| SNP_A-1751567 | 4917 | 0.415 | 0.63 | rs2371356 | 12 | q23.1 | NM_152905 | 0.4861 | 0.4955 | 0.4819 |
| SNP_A-1661932 | 924 | 0.436 | 0.62 | rs1566182 | 6 | q23.1 | NM_052913 | 0.2098 | 0.3866 | 0.4955 |
| SNP_A-1661139 | 884 | 0.383 | 0.57 | rs564310 | 2 | p23.1 | NM_000348 | 0.477 | 0.4997 | 0.4955 |
| SNP_A-1703083 | 2751 | 0.345 | 0.55 | rs953654 | 1 | p31.3 | NM_032852 | 0.4657 | 0.4592 | 0.4861 |
| SNP_A-1699451 | 2567 | 0.491 | 0.54 | rs554653 | 6 | p25.1 | NM_000129 | 0.2276 | 0.4717 | 0.4974 |
| SNP_A-1690872 | 2174 | 0.365 | 0.52 | rs207613 | 2 | p22.1 | NM_021097 | 0.4274 | 0.3628 | 0.4929 |
| SNP_A-1705477 | 2834 | 0.442 | 0.5 | rs953183 | 7 | q22.3 | NM_002649 | 0.4898 | 0.4898 | 0.4955 |
| SNP_A-1662918 | 977 | 0.333 | 0.49 | rs654559 | 6 | q15 | NM_000865 | 0.4997 | 0.3977 | 0.4819 |
| SNP_A-1660523 | 856 | 0.358 | 0.48 | rs15433193 | 8 | q21.12 | NM_000318 | 0.4274 | 0.477 | 0.4997 |
| SNP_A-1721678 | 3576 | 0.404 | 0.48 | rs929689 | 2 | p16.1 | NM_004105 | 0.4521 | 0.4274 | 0.4997 |
| SNP_A-1699721 | 2581 | 0.392 | 0.46 | rs951300 | 3 | q25.1 | NM_016094 | 0.4861 | 0.4997 | 0.4997 |
| SNP_A-1674163 | 1458 | 0.4 | 0.46 | rs1905444 | 12 | q15 | NM_003583 | 0.3628 | 0.1528 | 0.4955 |
| SNP_A-1692502 | 2235 | 0.404 | 0.45 | rs1890035 | 1 | q25.2 | NM_033127 | 0.4717 | 0.4274 | 0.4929 |
| SNP_A-1736715 | 4273 | 0.396 | 0.45 | rs1342947 | 1 | q23.1 | NM_001004473 | 0.4929 | 0.4974 | 0.4929 |
| SNP_A-1672534 | 1387 | 0.451 | 0.45 | rs1374284 | 2 | q13 | NM_014440 | 0.1528 | 0.4521 | 0.4592 |

FIG. 11A

| SNP | Index SNP | PercHetin Test | Selection Rate | dbSNPSID | Chrom | Cytoband | Associated Gene | Het_Asian | Het_AfAm | Het_Cauc |
|---|---|---|---|---|---|---|---|---|---|---|
| SNP_A-1710141 | 3037 | 0.38 | 0.45 | rs2203657 | 8 | q12.3 | NM_032467 | 0.477 | 0.4819 | 0.4955 |
| SNP_A-1675712 | 1522 | 0.407 | 0.45 | rs726402 | 12 | q12 | NM_175038 | 0.4521 | 0.4929 | 0.4861 |
| SNP_A-1658134 | 731 | 0.372 | 0.45 | rs1509577 | 2 | p23.1 | NM_016061 | 0.4521 | 0.375 | 0.495 |
| SNP_A-1645724 | 179 | 0.4 | 0.44 | rs958564 | 1 | q25.3 | NM_006469 | 0.4898 | 0.4898 | 0.4929 |
| SNP_A-1740777 | 4447 | 0.388 | 0.44 | rs3847126 | 7 | q34 | NM_080660 | 0.4657 | 0.4819 | 0.4997 |
| SNP_A-1672050 | 1354 | 0.471 | 0.43 | rs950487 | 1 | q23.1 | NM_001004473 | 0.4929 | 0.4974 | 0.4929 |
| SNP_A-1728265 | 3875 | 0.412 | 0.41 | rs950338 | 1 | q21.3 | NM_178354 | 0.4974 | 0.3977 | 0.4974 |
| SNP_A-1749587 | 4826 | 0.364 | 0.41 | rs1876054 | 4 | q28.3 | NM_020815 | 0.4955 | 0.4717 | 0.4657 |
| SNP_A-1757129 | 5137 | 0.37 | 0.41 | rs4131751 | 12 | q23.3 | NM_000980 | 0.1327 | 0.2276 | 0.4657 |
| SNP_A-1747691 | 4742 | 0.382 | 0.41 | rs1935571 | 1 | p21.3 | ENST00000358225 | 0.375 | 0.4893 | 0.4989 |
| SNP_A-1744257 | 4594 | 0.37 | 0.4 | rs1986626 | 8 | q24.3 | NM_152888 | 0.3628 | 0.4274 | 0.4974 |
| SNP_A-1660713 | 866 | 0.407 | 0.38 | rs1515561 | 12 | q22 | NM_001004330 | 0.4521 | 0.4717 | 0.4861 |
| SNP_A-1735979 | 4234 | 0.345 | 0.37 | rs1380416 | 1 | p22.2 | NM_198460 | 0.3367 | 0.4181 | 0.4955 |

FIG. 11B

| | A | B | D | E | F | G | H |
|---|---|---|---|---|---|---|---|
| 1 | #SNP rs# | PROD_SIZE | Chrom | Cytoband | Alleles | Primer | Sequence |
| 2 | rs967968 | 189 | 2 | p15 | C/G | P1R | GCAATCCTCCCTCCTTTCT |
| 3 | | | | | | P1La | AGCCAGAATTCACAGAATTAGTCCAC |
| 4 | | | | | | P1Lb | AGCCAGAATTCACAGAATTAGTCCAG |
| 5 | rs718015 | 282 | 7 | p14.1 | G/T | P2R | CTCTGTGCATCCCTCTGTCA |
| 6 | | | | | | P2La | TGATCTTCTAAGTTTTCAGAAAGCAG |
| 7 | | | | | | P2Lb | TGATCTTCTAAGTTTTCAGAAAGCAT |
| 8 | rs654559 | 382 | 6 | q15 | A/T | P3R | TTCTGCTTGCAGGACTTCAG |
| 9 | | | | | | P3La | CCCAGAGGTGTAGGAATGAGA |
| 10 | | | | | | P3Lb | CCCAGAGGTGTAGGAATGAGT |
| 11 | rs723725 | 479 | 7 | p21.1 | C/G | P4R | TGACAGATTTCGGCATTGA |
| 12 | | | | | | P4La | ATCCCACTCTGATGAGACTAGAATC |
| 13 | | | | | | P4Lb | ATCCCACTCTGATGAGACTAGAATG |
| 14 | rs487616 | 220 | 1 | q31.1 | A/T | P5R | TGGCACATGCCTGTAGTCTC |
| 15 | | | | | | P5La | ATACCCTGAGGCTCTGCAACATAA |
| 16 | | | | | | P5Lb | ATACCCTGAGGCTCTGCAACATAT |
| 17 | rs1935571 | 283 | 1 | p21.3 | G/T | P6R | ATTCACCTTCTGGGTTGAAA |
| 18 | | | | | | P6La | GTACATCAGCCTTCACTCAACAG |
| 19 | | | | | | P6Lb | GTACATCAGCCTTCACTCAACAT |
| 20 | rs2414908 | 385 | 15 | q22.31 | A/G | P7R | TGTCCAGCCATAGGAAAGG |
| 21 | | | | | | P7La | TCCCTCTTGCTGTCTTGCTC |
| 22 | | | | | | P7Lb | TCCCTCTTGCTGTCTTGCTT |
| 23 | rs1890035 | 482 | 1 | q25.2 | A/C | P8R | GGACAAAGACCCAAACAAGG |
| 24 | | | | | | P8La | CCCATTAAACATATGCAAATGGA |
| 25 | | | | | | P8Lb | CCCATTAAACATATGCAAATGGC |
| 26 | rs554653 | 220 | 6 | p25.1 | G/T | P9R | ACCACCGATGACTTGCCTAC |
| 27 | | | | | | P9La | ATTGGCGGGTACATGCG |
| 28 | | | | | | P9Lb | ATTGGCGGGTACATGCT |

FIG. 14 page 1 of 4

| | A | B | D | E | F | G | H |
|---|---|---|---|---|---|---|---|
| 1 | #SNP rs# | PROD_SIZE | Chrom | Cytoband | Alleles | Primer | Sequence |
| 29 | rs2254896 | 294 | 14 | q11.2 | A/G | P10R | GCTGAGGGCTGCAGTAGTTT |
| 30 | | | | | | P10La | GCATGTGATTTCTCTCTTTGGA |
| 31 | | | | | | P10Lb | GCATGTGATTTCTCTCTTTGGG |
| 32 | rs722152 | 410 | 12 | q22 | C/T | P11R | TCACCTGCTTCCCTAACTCC |
| 33 | | | | | | P11La | GCTAGTAAATCATATACAAATAAGAAAGA |
| 34 | | | | | | P11Lb | GCTAGTAAATCATATACAAATAAGAAAGG |
| 35 | rs1951096 | 486 | 14 | q32.2 | C/T | P12R | ACCTCGCCATTGTAATGCTC |
| 36 | | | | | | P12La | AAATGCATTTTTTCAAGCACTTC |
| 37 | | | | | | P12Lb | AAATGCATTTTTTCAAGCACTTT |
| 38 | rs953654 | 221 | 1 | p31.3 | C/T | P13R | GCAGGATGTTCTTGAGAAGG |
| 39 | | | | | | P13La | GAAGTAGTGGTTATATAACTAAGAC |
| 40 | | | | | | P13Lb | GAAGTAGTGGTTATATAACTAAGAT |
| 41 | rs1157158 | 314 | 5 | p15.31 | A/G | P14R | GTTCGGGGAGGGAAGACTAT |
| 42 | | | | | | P14La | CAAAAATTCTGAGGAAAAAAC |
| 43 | | | | | | P14Lb | CAAAAATTCTGAGGAAAAAAT |
| 44 | rs953183 | 419 | 7 | q22.3 | A/G | P15R | ATCTCGTGATTCACCCACCT |
| 45 | | | | | | P15La | ATGACAAAGGAGTCTTAGGTTTC |
| 46 | | | | | | P15Lb | ATGACAAAGGAGTCTTAGGTTTT |
| 47 | rs2203657 | 488 | 8 | q12.3 | A/G | P16R | ACTTGTTTCCAGCCTTTCA |
| 48 | | | | | | P16La | CAAGCCACACTGAAAACCAA |
| 49 | | | | | | P16Lb | CAAGCCACACTGAAAACCAG |
| 50 | rs2249248 | 227 | 21 | q22.2 | A/G | P17R | CTGCATCCTTTCCCACTGT |
| 51 | | | | | | P17La | CAGAAGAAAGCTCCTGCCA |
| 52 | | | | | | P17Lb | AGAAAGAAAGCTCCTGCCG |
| 53 | rs1515561 | 315 | 12 | q22 | C/G | P18R | TGAACTCCTGAGTGGACTGC |
| 54 | | | | | | P18La | CATTATAAATACAACTCATAAGATAGATTC |
| 55 | | | | | | P18Lb | CATTATAAATACAACTCATAAGATAGATTG |

FIG. 14 page 2 of 4

| | A | B | D | E | F | G | H |
|---|---|---|---|---|---|---|---|
| 1 | #SNP rs# | PROD_SIZE | Chrom | Cytoband | Alleles | Primer | Sequence |
| 56 | rs1564935 | 423 | 2 | q21.2 | C/T | P19R | TACCGATGTAGGCCAAGGAC |
| 57 | | | | | | P19La | CAGTTTATGCTCTGATAATGTTCAGAC |
| 58 | | | | | | P19Lb | CAGTTTATGCTCTGATAATGTTCAGAT |
| 59 | rs1876054 | 514 | 4 | q28.3 | C/T | P20R | TTCCAGCATGTACCAAATG |
| 60 | | | | | | P20La | ATACTCCCCAAATCTGGATCTACA |
| 61 | | | | | | P20Lb | ATACTCCCCAAATCTGGATCTACG |
| 62 | rs1342947 | 237 | 1 | q23.1 | A/G | P21R | CATTCACTTGTGCCCATTG |
| 63 | | | | | | P21La | CAGAATCTAGATAAAGAACACATTAA |
| 64 | | | | | | P21Lb | CAGAATCTAGATAAAGAACACATTAG |
| 65 | rs2868931 | 322 | 18 | p11.22 | A/T | P22R | AGAGTTGGCAAACACCAAGC |
| 66 | | | | | | P22La | CTTCCAGTTTTGATGGGACA |
| 67 | | | | | | P22Lb | CTTCCAGTTTTGATGGGACT |
| 68 | rs1543193 | 424 | 8 | q21.12 | A/T | P23R | GGCCAGGAACTCACTCTTTG |
| 69 | | | | | | P23La | CCTCAGATGCATGTCTTTCTAA |
| 70 | | | | | | P23Lb | CCTCAGATGCATGTCTTTTCTAT |
| 71 | rs951300 | 519 | 3 | q25.1 | A/G | P24R | TTCGCCCATTATGGTATGTC |
| 72 | | | | | | P24La | AACTTACTACTCAGTCTTCTCTGTACTTAC |
| 73 | | | | | | P24Lb | ATAACTTACTACTCAGTCTTCTCTGTACTTAT |
| 74 | | | | | | | |
| 75 | | | | | | | |
| 76 | | | | | | | |
| 77 | | | | | | | |
| 78 | rs3847126 | 501 | 7 | q34 | A/G | P4.2R | TTATTCCCACCTCGTCTTG |
| 79 | | | | | | P4.2La | TTTGCAAGGTGCTCGTGAA |

FIG. 14 page 3 of 4

| | A | B | D | E | F | G | H |
|---|---|---|---|---|---|---|---|
| 1 | #SNP rs# | PROD_SIZE | Chrom | Cytoband | Alleles | Primer | Sequence |
| 80 | | | | | | P4.2Lb | TTTGCAAGGTGCTCGTGAG |
| 81 | rs3847896 | 283 | 12 | p12.1 | C/T | P14.2R | GAGACTGGCAGACTGCAAAA |
| 82 | | | | | | P14.2La | GAGTGAGTGGTAAGTGTAAACTTAGCC |
| 83 | | | | | | P14.2Lb | GAGTGAGTGGTAAGTGTAAACTTAGCT |
| 84 | rs1986626 | 481 | 8 | q24.3 | A/G | P16.2R | TCTCTGGTGAGTGGTATGTTCAA |
| 85 | | | | | | P16.2La | GTGCTGACCTTTGGAAAGTGA |
| 86 | | | | | | P16.2Lb | GTGCTGACCTTTGGAAAGTGG |
| 87 | rs1509577 | 484 | 2 | p23.1 | C/G | P20.2R | TTATGTTCCCTCCCTCCAGA |
| 88 | | | | | | P20.2La | ACTGTTTAAGCCATGCTAATATACATC |
| 89 | | | | | | P20.2Lb | ACTGTTTAAGCCATGCTAATATACATG |

FIG. 14 page 4 of 4 rs967968

AGCCAGAATTCACAGAATTAGTCCA[C/G]ACAGGTAGCCAACAAACAAAACACA rs718015

TGATCTTCTAAGTTTTCAGAAAGCA[G/T]TACCTTTTCCATAAGCATCTGTTTA rs654559

TTGATTCATTGGAGGTCTTTATGCT[A/T]CTCATTCCTACACCTCTGGGCTTTG rs723725

AATCCCACTCTGATGAGACTAGAAT[C/G]AATTAACTCCAGTGCCTAATACACA rs487616

AGATACCCTGAGGCTCTGCAACATA[A/T]CCATTCAGAATATGGGAGCTACTTA rs1935571

AATGTACATCAGCCTTCACTCAACA[G/T]TAGTTTTTGTTTCATGGTGTACATT rs2414908 cgtggcagctggttttcttcaggac[A/G]agcaagacagcaagagggagcaagc rs1890035

TCCCCCATTAAACATATGCAAATGG[A/C]AATGGTAATAAACTCAGATAATGAT rs554653

TCCCCCATTAAACATATGCAAATGG[A/C]AATGGTAATAAACTCAGATAATGAT rs554653

TCTGCAGGCATTGGCGGGTACATGC[G/T]GATCATAACCACCAGATGGCGCTGT

FIG. 15 page 1 of 3 rs2254896 tgtggcatgtgatttctctctttgg[A/G]tatcaaggtctggtagaacaaacgg rs2868931

ATGTGTGATTTCACCATCTCAAAGT[C/T]CTTTCTTATTTGTATATGATTTACT rs1951096

CAAAATGCATTTTTTTCAAGCACTT[C/T]AAACTTCATAAACTTGGGTGTACAT rs953654 tgaagtagtggttatataactaaga[C/T]gctcaTTAAATGATGATACCCACGT rs1157158

CTCTAGAAGATAGATGTAAAGCTTC[A/G]TTTTTTTTCCTCAGAATTTTGAAT rs953183

TTGAACAACCCTAGACTTTTTCAGC[A/G]AAACCCTAAGACTCCTTTGTCATCC rs2203657 gtcattcaagccacactgaaaacca[A/G]aactaagaaatactttcaagcatct rs2249248

TCCATTCAGAAAGAAAGCTCCTGCC[A/G]TGTGTTCACTCTATTTAAATGATGA rs1515561

TTTCTTAACAAATCTTTTTCCCGTT[C/G]AATCTATCTTATGAGTTGTATTTAT rs1564935

AGTTTATGCTCTGATAATGTTCAGA[C/T]ATCCAGTTATAGAGCTATCAGTATC rs1876054

TGAGAAATTTACATCCAGGCACTAT[C/T]GTAGATCCAGATTTTGGGGAGTATG rs1342947

GAATCTAGATAAAAGAACACATTTA[A/G]GCAAGAGGTAGCACAGAATAAGAAT rs2868931 caaaacttccagttttttgatgggac[A/T]tggctgcctagaataaagatatttc rs1543193

AGTCTTGAGCTAGGAGACTAAGTGG[A/T]TAGAAAAGACATGCATCTGAGGGCA rs951300

AAAGAAGATACTTAATCAAATTCAT[A/G]TAAGTACAGAGAAGACTGAGTAAGT rs3847126

CTGCTATTTTGCAAGGTGCTCGTGA[A/G]GATTAAATGCATTAATGTCATGTAA rs3847896

AGTGAGTGGTAAGTGTAAACTTAGC[C/T]GGAAAGCCCACATAGCAAGAAAGCA rs1986626 taatggtgctgacctttggaaagtg[A/G]tgtcttgactggaaactggaagatt rs1509577 tgttttaagccatgctaaTATACAT[C/G]GCTTGGAGTTTGTTAGATCTAGGTA

FIG. 15 page 3 of 3

SEQUENCE LISTING

```
<160> NUMBER OF SEQ ID NOS: 113

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gcaatcctcc ctcctttct                                               20

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
agccagaatt cacagaatta gtccac                                       26
```

-continued

```
<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
agccagaatt cacagaatta gtccag                                          26

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctctgtgcat ccctctgtca                                                 20

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
tgatcttcta agttttcaga aagcag                                          26

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
tgatcttcta agttttcaga aagcat                                          26

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ttctgcttgc aggacttcag                                                 20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
cccagaggtg taggaatgag a                                               21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
```

-continued

```
cccagaggtg taggaatgag t                                      21

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tgacagattt tcggcattga                                        20

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
atcccactct gatgagacta gaatc                                  25

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
atcccactct gatgagacta gaatg                                  25

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tggcacatgc ctgtagtctc                                        20

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14 atacccctgag gctctgcaac ataa                                  24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ataccctgag gctctgcaac atat                                   24

<210> SEQ ID NO 16
<211> LENGTH: 20
<212> TYPE: DNA
<213> ORGANISM: Artificial Sequence
```

-continued

```
<220> FEATURE:
<223> OTHER INFORMATION: Primer

<400> SEQUENCE: 16
attcaccttc tgggttgaaa                                                    20

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
gtacatcagc cttcactcaa cag                                                23

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
gtacatcagc cttcactcaa cat                                                23

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tgtccagcca taggaaaagg                                                    20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tccctcttgc tgtcttgctc                                                    20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
tccctcttgc tgtcttgctt                                                    20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ggacaaagac ccaaacaagg                                                    20
```

```
<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
cccattaaac atatgcaaat gga                                              23

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
cccattaaac atatgcaaat ggc                                              23

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
accaccgatg acttgcctac                                                  20

<210> SEQ ID NO 26
<211> LENGTH: 17
<212> TYPE: DNA
<213> ORGANISM: Artificial Sequence
<220> FEATURE:
<223> OTHER INFORMATION: Primer

<400> SEQUENCE: 26
attggcgggt acatgcg                                                     17

<210> SEQ ID NO 27
<211> LENGTH: 17
<212> TYPE: DNA
<213> ORGANISM: Artificial Sequence
<220> FEATURE:
<223> OTHER INFORMATION: Primer

<400> SEQUENCE: 27
attggcgggt acatgct                                                     17

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gctgagggct gcagtagttt                                                  20

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
```

-continued gcatgtgatt tctctctttg ga                                            22

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
gcatgtgatt tctctctttg gg                                            22

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tcacctgctt ccctaactcc                                               20

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
gctagtaaat catatacaaa taagaaaga                                     29

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
gctagtaaat catatacaaa taagaaagg                                     29

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
acctcgccat tgtaatgctc                                               20

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
aaatgcattt tttttcaagc acttc                                         25

<210> SEQ ID NO 36
<211> LENGTH: 24
<212> TYPE: DNA
<213> ORGANISM: Artificial Sequence

```
<220> FEATURE:
<223> OTHER INFORMATION: Primer

<400> SEQUENCE: 36
aaatgcattt ttttcaagca cttt                                          24

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gcaggatgtt cttgagaagg                                               20

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
gaagtagtgg ttatataact aagac                                         25

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
gaagtagtgg ttatataact aagat                                         25

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gttcggggag ggaagactat                                               20

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
caaaaattct gaggaaaaaa aac                                           23

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
caaaaattct gaggaaaaaa aat                                           23
```

```
<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
atctcgtgat tcacccacct                                               20

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
atgacaaagg agtcttaggg tttc                                          24

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
atgacaaagg agtcttaggg tttt                                          24

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
acttgtttcc agcctttcca                                               20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
caagccacac tgaaaaccaa                                               20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
caagccacac tgaaaaccag                                               20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
```
ctgcatcctt ttcccactgt                                              20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
cagaaagaaa gctcctgcca                                              20

<210> SEQ ID NO 51
<211> LENGTH: 19
<212> TYPE: DNA
<213> ORGANISM: Artificial Sequence
<220> FEATURE:
<223> OTHER INFORMATION: Primer

<400> SEQUENCE: 51
agaaagaaag ctcctgccg                                               19

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tgaactcctg agtggactgc                                              20

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
cattataaat acaactcata agatagattc                                   30

<210> SEQ ID NO 54
<211> LENGTH: 30
<212> TYPE: DNA
<213> ORGANISM: Artificial Sequence
<220> FEATURE:
<223> OTHER INFORMATION: Primer

<400> SEQUENCE: 54
cattataaat acaactcata agatagattg                                   30

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
taccgatgta ggccaaggac                                              20

<210> SEQ ID NO 56
<211> LENGTH: 27
<212> TYPE: DNA
<213> ORGANISM: Artificial Sequence

```
<220> FEATURE:
<223> OTHER INFORMATION: Primer

<400> SEQUENCE: 56
cagtttatgc tctgataatg ttcagac                                      27

<210> SEQ ID NO 57
<211> LENGTH: 27
<212> TYPE: DNA
<213> ORGANISM: Artificial Sequence
<220> FEATURE:
<223> OTHER INFORMATION: Primer

<400> SEQUENCE: 57
cagtttatgc tctgataatg ttcagat                                      27

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ttccagcatg ctaccaaatg                                              20

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
atactcccca aaatctggat ctaca                                        25

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
atactcccca aaatctggat ctacg                                        25

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
cattcacttg ttgcccattg                                              20

<210> SEQ ID NO 62
<211> LENGTH: 28
<212> TYPE: DNA
<213> ORGANISM: Artificial Sequence
<220> FEATURE:
<223> OTHER INFORMATION: Primer

<400> SEQUENCE: 62
cagaatctag ataaaagaac acatttaa                                     28
```

```
<210> SEQ ID NO 63
<211> LENGTH: 28
<212> TYPE: DNA
<213> ORGANISM: Artificial Sequence
<220> FEATURE:
<223> OTHER INFORMATION: Primer

<400> SEQUENCE: 63
cagaatctag ataaaagaac acatttag                                    28

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
agagttggca aaccacaagc                                             20

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cttccagttt ttgatgggac a                                           21

<210> SEQ ID NO 66
<211> LENGTH: 21
<212> TYPE: DNA
<213> ORGANISM: Artificial Sequence
<220> FEATURE:
<223> OTHER INFORMATION: Primer

<400> SEQUENCE: 66
cttccagttt ttgatgggac t                                           21

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
ggccaggaac tcactctttg                                             20

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
cctcagatgc atgtcttttc taa                                         23

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69
```

```
cctcagatgc atgtcttttc tat                                          23
```

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70

```
ttcgcccatt atggtatgtc                                              20
```

<210> SEQ ID NO 71
<211> LENGTH: 27
<212> TYPE: DNA
<213> ORGANISM: Artificial Sequence
<220> FEATURE:
<223> OTHER INFORMATION: Primer

<400> SEQUENCE: 71

```
aacttactca gtcttctctg tacttac                                      27
```

<210> SEQ ID NO 72
<211> LENGTH: 29
<212> TYPE: DNA
<213> ORGANISM: Artificial Sequence
<220> FEATURE:
<223> OTHER INFORMATION: Primer

<400> SEQUENCE: 72

```
ataacttact cagtcttctc tgtacttat                                    29
```

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73

```
ttattcccca cctcgtcttg                                              20
```

<210> SEQ ID NO 74
<211> LENGTH: 19
<212> TYPE: DNA
<213> ORGANISM: Artificial Sequence
<220> FEATURE:
<223> OTHER INFORMATION: Primer

<400> SEQUENCE: 74

```
tttgcaaggt gctcgtgaa                                               19
```

<210> SEQ ID NO 75
<211> LENGTH: 19
<212> TYPE: DNA
<213> ORGANISM: Artificial Sequence
<220> FEATURE:
<223> OTHER INFORMATION: Primer

<400> SEQUENCE: 75

```
tttgcaaggt gctcgtgag                                               19
```

<210> SEQ ID NO 76
<211> LENGTH: 20
<212> TYPE: DNA
<213> ORGANISM: Artificial Sequence

```
<220> FEATURE:
<223> OTHER INFORMATION: Primer

<400> SEQUENCE: 76
gagactggca gactgcaaaa                                              20

<210> SEQ ID NO 77
<211> LENGTH: 27
<212> TYPE: DNA
<213> ORGANISM: Artificial Sequence
<220> FEATURE:
<223> OTHER INFORMATION: Primer

<400> SEQUENCE: 77
gagtgagtgg taagtgtaaa cttagcc                                      27

<210> SEQ ID NO 78
<211> LENGTH: 27
<212> TYPE: DNA
<213> ORGANISM: Artificial Sequence
<220> FEATURE:
<223> OTHER INFORMATION: Primer

<400> SEQUENCE: 78
gagtgagtgg taagtgtaaa cttagct                                      27

<210> SEQ ID NO 79
<211> LENGTH: 23
<212> TYPE: DNA
<213> ORGANISM: Artificial Sequence
<220> FEATURE:
<223> OTHER INFORMATION: Primer

<400> SEQUENCE: 79
tctctggtga gtggtatgtt caa                                          23

<210> SEQ ID NO 80
<211> LENGTH: 21
<212> TYPE: DNA
<213> ORGANISM: Artificial Sequence
<220> FEATURE:
<223> OTHER INFORMATION: Primer

<400> SEQUENCE: 80
gtgctgacct ttggaaagtg a                                            21

<210> SEQ ID NO 81
<211> LENGTH: 21
<212> TYPE: DNA
<213> ORGANISM: Artificial Sequence
<220> FEATURE:
<223> OTHER INFORMATION: Primer

<400> SEQUENCE: 81
gtgctgacct ttggaaagtg g                                            21

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
ttatgttccc tccctccaca                                              20
```

-continued

<210> SEQ ID NO 83
<211> LENGTH: 28
<212> TYPE: DNA
<213> ORGANISM: Artificial Sequence
<220> FEATURE:
<223> OTHER INFORMATION: Primer

<400> SEQUENCE: 83
actgttttaa gccatgctaa tatacatc                               28

<210> SEQ ID NO 84
<211> LENGTH: 28
<212> TYPE: DNA
<213> ORGANISM: Artificial Sequence
<220> FEATURE:
<223> OTHER INFORMATION: Primer

<400> SEQUENCE: 84
actgttttaa gccatgctaa tatacatg                               28

<210> SEQ ID NO 85
<211> LENGTH: 51
<212> TYPE: DNA
<213> ORGANISM: Homo sapiens

<400> SEQUENCE: 85
agccagaatt cacagaatta gtccasacag gtagccaaca aacaaaacac a     51

<210> SEQ ID NO 86
<211> LENGTH: 51
<212> TYPE: DNA
<213> ORGANISM: Homo sapiens

<400> SEQUENCE: 86
tgatcttcta agttttcaga aagcaktacc ttttccataa gcatctgttt a     51

<210> SEQ ID NO 87
<211> LENGTH: 51
<212> TYPE: DNA
<213> ORGANISM: Homo sapiens

<400> SEQUENCE: 87
ttgattcatt ggaggtcttt atgctwctca ttcctacacc tctgggcttt g     51

<210> SEQ ID NO 88
<211> LENGTH: 51
<212> TYPE: DNA
<213> ORGANISM: Homo sapiens

<400> SEQUENCE: 88
aatcccactc tgatgagact agaatsaatt aactccagtg cctaatacac a     51

<210> SEQ ID NO 89
<211> LENGTH: 51
<212> TYPE: DNA
<213> ORGANISM: Homo sapiens

<400> SEQUENCE: 89
agataccctg aggctctgca acatawccat tcagaatatg ggagctactt a     51

<210> SEQ ID NO 90
<211> LENGTH: 51
<212> TYPE: DNA
<213> ORGANISM: Homo sapiens

<400> SEQUENCE: 90
aatgtacatc agccttcact caacaktagt ttttgtttca tggtgtacat t    51

<210> SEQ ID NO 91
<211> LENGTH: 51
<212> TYPE: DNA
<213> ORGANISM: Homo sapiens

<400> SEQUENCE: 91
cgtggcagct ggttttcttc aggacragca agacagcaag agggagcaag c    51

<210> SEQ ID NO 92
<211> LENGTH: 51
<212> TYPE: DNA
<213> ORGANISM: Homo sapiens

<400> SEQUENCE: 92
tcccccatta aacatatgca aatggmaatg gtaataaact cagataatga t    51

<210> SEQ ID NO 93
<211> LENGTH: 51
<212> TYPE: DNA
<213> ORGANISM: Homo sapiens

<400> SEQUENCE: 93
tcccccatta aacatatgca aatggmaatg gtaataaact cagataatga t    51

<210> SEQ ID NO 94
<211> LENGTH: 51
<212> TYPE: DNA
<213> ORGANISM: Homo sapiens

<400> SEQUENCE: 94
tctgcaggca ttggcgggta catgckgatc ataaccacca gatggcgctg t    51

<210> SEQ ID NO 95
<211> LENGTH: 51
<212> TYPE: DNA
<213> ORGANISM: Homo sapiens

<400> SEQUENCE: 95
tgtggcatgt gatttctctc tttggrtatc aaggtctggt agaacaaacg g    51

<210> SEQ ID NO 96
<211> LENGTH: 51
<212> TYPE: DNA
<213> ORGANISM: Homo sapiens

<400> SEQUENCE: 96
atgtgtgatt tcaccatctc aaagtycttt cttatttgta tatgatttac t    51

<210> SEQ ID NO 97
<211> LENGTH: 51
<212> TYPE: DNA
<213> ORGANISM: Homo sapiens

<400> SEQUENCE: 97
caaaatgcat ttttttcaag cacttyaaac ttcataaact tgggtgtaca t    51

<210> SEQ ID NO 98
<211> LENGTH: 51
<212> TYPE: DNA
<213> ORGANISM: Homo sapiens

<400> SEQUENCE: 98
tgaagtagtg gttatataac taagaygctc attaaatgat gatacccacg t    51

<210> SEQ ID NO 99
<211> LENGTH: 51
<212> TYPE: DNA
<213> ORGANISM: Homo sapiens

<400> SEQUENCE: 99
ctctagaaga tagatgtaaa gcttcrtttt ttttcctcag aattttgaa t    51

<210> SEQ ID NO 100
<211> LENGTH: 51
<212> TYPE: DNA
<213> ORGANISM: Homo sapiens

<400> SEQUENCE: 100
ttgaacaacc ctagactttt tcagcraaac cctaagactc ctttgtcatc c    51

<210> SEQ ID NO 101
<211> LENGTH: 51
<212> TYPE: DNA
<213> ORGANISM: Homo sapiens

<400> SEQUENCE: 101
gtcattcaag ccacactgaa aaccaraact aagaaatact ttcaagcatc t    51

<210> SEQ ID NO 102
<211> LENGTH: 51
<212> TYPE: DNA
<213> ORGANISM: Homo sapiens

<400> SEQUENCE: 102
tccattcaga aagaaagctc ctgccrtgtg ttcactctat ttaaatgatg a    51

<210> SEQ ID NO 103
<211> LENGTH: 51
<212> TYPE: DNA
<213> ORGANISM: Homo sapiens

<400> SEQUENCE: 103
tttcttaaca aatctttttc ccgttsaatc tatcttatga gttgtattta t    51

<210> SEQ ID NO 104
<211> LENGTH: 51
<212> TYPE: DNA
<213> ORGANISM: Homo sapiens

<400> SEQUENCE: 104
agtttatgct ctgataatgt tcagayatcc agttatagag ctatcagtat c    51

<210> SEQ ID NO 105
<211> LENGTH: 51
<212> TYPE: DNA
<213> ORGANISM: Homo sapiens

<400> SEQUENCE: 105
tgagaaattt acatccaggc actatygtag atccagattt tggggagtat g    51

<210> SEQ ID NO 106
<211> LENGTH: 51
<212> TYPE: DNA
<213> ORGANISM: Homo sapiens

<400> SEQUENCE: 106

```
gaatctagat aaaagaacac atttargcaa gaggtagcac agaataagaa t          51
```

<210> SEQ ID NO 107
<211> LENGTH: 51
<212> TYPE: DNA
<213> ORGANISM: Homo sapiens

<400> SEQUENCE: 107

```
caaaacttcc agttttgat gggacwtggc tgcctagaat aaagatattt c           51
```

<210> SEQ ID NO 108
<211> LENGTH: 51
<212> TYPE: DNA
<213> ORGANISM: Homo sapiens

<400> SEQUENCE: 108

```
agtcttgagc taggagacta agtggwtaga aaagacatgc atctgagggc a          51
```

<210> SEQ ID NO 109
<211> LENGTH: 51
<212> TYPE: DNA
<213> ORGANISM: Homo sapiens

<400> SEQUENCE: 109

```
aaagaagata cttaatcaaa ttcatrtaag tacagagaag actgagtaag t          51
```

<210> SEQ ID NO 110
<211> LENGTH: 51
<212> TYPE: DNA
<213> ORGANISM: Homo sapiens

<400> SEQUENCE: 110

```
ctgctatttt gcaaggtgct cgtgargatt aaatgcatta atgtcatgta a          51
```

<210> SEQ ID NO 111
<211> LENGTH: 51
<212> TYPE: DNA
<213> ORGANISM: Homo sapiens

<400> SEQUENCE: 111

```
agtgagtggt aagtgtaaac ttagcyggaa agcccacata gcaagaaagc a          51
```

<210> SEQ ID NO 112
<211> LENGTH: 51
<212> TYPE: DNA
<213> ORGANISM: Homo sapiens

<400> SEQUENCE: 112

```
taatggtgct gacctttgga aagtgrtgtc ttgactggaa actggaagat t          51
```

<210> SEQ ID NO 113
<211> LENGTH: 51
<212> TYPE: DNA
<213> ORGANISM: Homo sapiens

<400> SEQUENCE: 113

```
tgttttaagc catgctaata tacatsgctt ggagtttgtt agatctaggt a          51
```

METHODS FOR IDENTIFYING AND USING SNP PANELS

CLAIM OF PRIORITY

This application claims the benefit of U.S. Provisional Patent Application Ser. No. 60/812,477, filed on Jun. 9, 2006, the entire contents of which are hereby incorporated by reference.

GOVERNMENT SUPPORT

The work described herein was supported, at least in part, by a grant from the National Institutes of Health (AG022404). The United States Government has certain rights in this invention.

BACKGROUND

Because cancer and many other diseases have a genetic basis, and because a patient's response to a particular drug or treatment can be influenced by the patient's genetic makeup, researchers have undertaken the task of genetically characterizing patient tissue samples (including tumor samples), cell lines, and xenografts.

A population of organisms will contain several variants (alleles) of a given gene. Alleles can differ from one another at single basepair. These single basepair differences are called single nucleotide polymorphisms (SNPs), and several can be present in a single gene. High-throughput genotyping methods using high-density nucleic acid arrays and other methods can accurately genotype (i.e., determine the nucleotide(s) present) hundreds or thousands of SNPs in a genetic sample in parallel to provide an unequivocal molecular fingerprint of the genetic sample. The somatic cells of diploid organisms have two copies of each autosomal gene and many high throughput genotyping techniques are be sensitive enough to analyze a SNP to determine if an individual is homozygous for a first allele, homozygous for a second allele, or heterozygous (i.e., possesses one copy of each allele). The results of this analysis can be used for research and for making diagnostic and therapeutic decisions.

The value of genetic analysis for research, diagnosis and treatment depends on the accuracy of the analysis. For example, potential therapeutic agents for treatment of cancer are sometimes identified by screening in cancer cells lines. Thus, it is crucial that the cell lines used in such analysis are properly identified. In addition, normal and tumor samples taken from cancer patient are used in staging, diagnoses, selecting treatments and monitoring the effect of treatments. Thus, the accurate identification of samples is extremely important because mis-identification can lead to an incorrect diagnosis or selection of a sub-optimal therapy.

Methods are available for genotyping hundreds or thousands of SNPs in parallel, and these methods can be used for proper identification of samples. However, particularly where a large number of samples must be analyzed, the genotyping of hundred or thousands of SNPs and the analysis of the resulting data can prove to be time-consuming and complex. Thus, it would be desirable to identify a manageable number of SNPs that, taken together, have the power to discriminate among and identify genetic samples.

SUMMARY

Described herein are methods and tools for accurately identifying and/or distinguishing biological samples containing genetic material, e.g., cell lines, tissue samples, blood samples, and the like. The methods are based, at least in part, on statistical analysis of genetic data, e.g., SNP genotype calls. When applied to particular sample datasets, e.g., a particular group of genetic samples, the methods described herein permit the identification of a relatively small set of SNPs that can be used as a powerful tool for identifying and/or distinguishing samples containing genetic material. The methods described herein permit the identification of sets of SNPs that are far more useful for distinguishing biological samples than much larger sets of randomly selected SNPs that are commonly used for genetic analysis. Because the number of SNPs required for genetic analysis is relatively small when using SNPs selected as described herein, the genetic analysis is very cost effective, particularly when compared to analysis that uses many hundreds or thousands of randomly selected SNPs, most of which are essentially useless for identification and discrimination of samples.

The methods described herein for selecting SNPs are particularly powerful because they can be used to select a set (panel) of SNPs that are tailored to the type of samples being analyzed. In many cases the actual SNPs selected will depend on the samples one wishes to analyze (e.g., whether the samples are from normal tissue or tumor tissue, the characteristics of the population of individuals from which the samples are obtained). For example, the methods described herein can be used to identify a set of SNPs that are useful for discriminating among the various cell types in the NCI60 cell lines. The methods described herein can also be used to identify a set of SNPs that are useful for discriminating among many thousands of cancer tumor samples. It is possible that the sets of SNPs selected in these two cases will not completely overlap. Indeed, there might be little overlap. In the methods described herein, actual analysis of the samples to be analyzed (or a subset of the actual samples to be analyzed) is used to determine which SNPs should be used for discrimination and identification of samples. This is as opposed to many other techniques, which rely on a priori selection methods.

Because the number of SNPs used in a SNP panel identified as described herein is relatively small, analysis of a genetic sample at each of the SNPs in a panel produces a result that can be thought of as a genetic barcode that identifies the biological sample. The barcode itself is series of genotypes at the SNPs in the panel, e.g., homozygous T at SNP 1, homozygous G at SNP 2, heterozygous A/T at SNP 3, etc. This genetic bar code can be compared to other genetic barcodes stored in a database. Each stored (or reference) genetic barcode is generated by analysis of an associated genetic sample. The genetic barcode (SNP genotype pattern) generated from a test genetic sample can be compared to the reference barcodes in order to identify a reference genetic barcode that exactly matches (or nearly matches) the test barcode. The test sample is very likely to be identical to (or genetically very closely related to) the genetic sample associated with matching barcode. Of course, the degree of confidence in the determination can depend on the SNPs analyzed and the number of SNPs analyzed. For SNPs of equal ability to discriminate among genetic samples, the larger number of SNPs analyzed, the great the confidence that a perfect match between two SNP panels means that the associated genetic samples are identical.

As noted above, the precise SNP panel used can vary from one application to another. Moreover, the number of SNPs in the panel can vary depending one the degree of confidence needed in the sample identification. For example, a first panel could be used to distinguish among NCI60 cell lines with a given degree of confidence. A second, larger panel could be used to distinguish among NCI60 cell lines with a far higher degree of confidence. The second panel could contain all of the SNPs in the first panel as well as additional SNPs. A different panel might be used to distinguish among samples in a collection of patient tissue samples, e.g., a collection of patient tissue samples used in a particular drug screening program.

Once a SNP panel has been identified, for example by analyzing a subset of a collection of biological samples, test biological samples can be analyzed to determine the genotype present at each SNP using techniques that are standard in the art. The vast majority of SNPs have two possible alleles and such SNPs are useful in the methods described herein. Thus, genetic material (DNA or cDNA) is obtained from a test biological sample and each selected SNP (i.e., each SNP in the panel) is analyzed to determine whether the test biological sample is homozygous for the first of the two possible alleles, homozygous for the second of the two possible alleles or heterozygous for the two possible alleles. In some cases, the analysis will not even require physically determining the genotype present at certain SNPs since the test biological sample will have been previously analyzed at some or all of the SNPs in the panel. Thus, the techniques described herein can be used to reanalyze samples that have already been genotyped at thousands of SNPs. In this reanalysis, only a subset of the informative SNPs, i.e., those identified by the techniques described herein are considered.

Described herein are methods for identifying at least one SNP useful for analyzing a genetic sample. The methods include:

(a) obtaining a population of selected genetic samples;

(b) separating, e.g., randomly dividing, the population of genetic samples into a first subpopulation of genetic samples including a portion of the genetic samples and a second subpopulation including the remaining genetic samples;

(c) analyzing the genotype at each SNP of a plurality of SNPs for each genetic sample in the first subpopulation of genetic samples to determine for each SNP:
  i) $N_{aa}$, the number of genetic samples in which the SNP is homozygous for a first allele,
  ii) $N_{bb}$, the number of genetic samples in which the SNP is homozygous for a second allele, and
  iii) $N_{ab}$, the number of genetic samples in which the SNP is heterozygous for a first and a second allele;

(d) for the genetic samples in the first subpopulation, ranking each SNP of the plurality of SNPs by how nearly the ratio $N_{aa}:N_{bb}:N_{ab}$ matches the ratio 1:1:2 to provide a ranking of SNPs;

(e) analyzing the genotype at each SNP in the plurality of SNPs for each genetic sample in the second subpopulation of genetic samples to determine for each SNP:
  i) $N'_{aa}$, the number of genetic samples in which the SNP is homozygous for a first allele,
  ii) $N'_{bb}$, the number of genetic samples in which the SNP is homozygous for a second allele, and
  iii) $N'_{ab}$, the number of genetic samples in which the SNP is heterozygous for a first and a second allele;

(f) for the genetic samples in the second subpopulation, determining how closely the ratio $N'_{aa}:N'_{bb}:N'_{ab}$ matches the ratio 1:1:2 to provide a score for each SNP;

(g) designating a SNP that both ranks above a pre-determined cut-off in the ranking when analyzed in the first subpopulation and has a score above a pre-determined score when analyzed in the second subpopulation as a candidate SNP;

(h) repeating steps (b)-(g) at least two times, each time designating one or more SNPs as a candidate SNP to generate at least two groups of candidate SNPs; and (i) identifying a SNP designated as a candidate SNP at least two times as a SNP useful for analyzing a genetic sample.

As noted above, the SNPs identified as useful for analyzing a genetic sample are particularly useful for analyzing a genetic sample that is (or is suspected of being) from the same biological source as a genetic sample in the population of selected genetic samples. Thus, the identified SNPs are particularly useful for determining whether a test genetic sample is from the same biological source as a genetic sample that is a member of the population of selected genetic samples. For example, the population of selected genetic samples can all be contributed by cancer patients at a particular institution. This population of genetic samples can be used to identify a group of SNPs, i.e., a SNP panel. The SNPs in this SNP panel will be particularly useful for determining whether a test genetic sample is from a patient that contributed to the population of genetic samples. In some cases, the identified SNPs can be used to analyze genetic samples that are not the same as or closely related to a genetic sample that is a member of the population of selected genetic samples.

Various statistical methods known to those of ordinary skill in the art can be used to score SNPs by how nearly the ratio $N_{aa}:N_{bb}:N_{ab}$ matches the ratio 1:1:2. In addition, various statistical methods can be used to score SNPs by how nearly the ratio $N_{aa}:N_{bb}:N_{ab}$ matches the ratio 1:1:2 to provide a ranking of SNPs. In both cases, the goal is to select those SNPs where the ratio $N_{aa}:N_{bb}:N_{ab}$ is extremely close to or exactly 1:1:2. For example, the ratio can differ by less than 5%, 3%, 2%, 1%, 0.5%, 0.1%, 0.01% or 0.001%.

In various embodiments of these methods, steps (b)-(g) can be repeated at least 5 or 10 or more times and wherein a SNP designated as a candidate SNP at least 10 times is identified as a SNP useful for analyzing a genetic sample. Of course, the steps can be repeated fewer or more times (e.g., 5, 20, 30, 40, 50, 100, 200, 300, 400, 500, 600, 700, 800, 900, or 1000 or more times), and a SNP designated as a candidate SNP fewer or more than 10 times (e.g., 5, 20, 30, 40, 50, 100, 200, 300, 400, 500, 600, 700, 800, 900, or 1000 or more times) is identified as a SNP useful for analyzing genetic samples. Generally, the number of times that the steps are repeated dictates how often a SNP must be designated as a candidate SNP. Thus, if the steps are repeated 1,000 times, SNPs designated as candidates 400, 500, 600, 800, or more times are identified as being useful. Generally, it will be desirable to use SNPs that are designated in at least 40%, 45%, 50%, 60%, 75%, 90%, or even 100% of the repetitions of the selection. A group of identified SNPs forms a potential SNP panel. Some or all of the SNPs in such a panel can be used together to analyze genetic samples.

The methods described herein can be used to identify multiple useful SNPs, e.g., at least 5, 10, 20, 30, 40, 50, 100, 200, 300, 400, 500, 600, 700, 800, 900, or 1000 useful SNPs. In general, when there are multiple rounds of steps (b)-(g), the SNPs designated most frequently are often the most useful for analyzing a genetic sample. Of course, this is not always the case. Some frequently designated SNPs are less useful for a variety of reasons. For example, a frequently designated SNP can be difficult or impractical to genotype. Thus, a SNP panel can exclude certain frequently designated SNPs.

Also described are methods for identifying a panel of SNPs useful for analyzing a genetic sample. The methods include:
(a) using a method described herein to identify a plurality of SNPs useful for analyzing a genetic sample;
(b) excluding at least one of the plurality of SNPs; and (c) identifying the remaining SNPs as a panel of SNPs useful for analyzing a genetic sample.

In some cases at least one SNP located in an intron is excluded, at least one SNP located in a region subject to loss of heterozygosity is excluded, at least one SNP having a heterozygosity rate that differs more than 2% between Caucasian and Asian populations is excluded, at least one SNP having a heterozygosity rate that differs more than 2% between Caucasian and African American populations is excluded, and/or at least one SNP having a heterozygosity rate that differs more than 2% between Asian and African American populations is excluded.

Also described herein are methods for analyzing a genetic sample. The methods include:
(a) obtaining a first genetic sample;
(b) analyzing the genotype of the genetic sample at each SNP in a set of SNPs identified as useful for analyzing genetic samples, wherein each SNP in the set of SNPs was identified as useful using a method described herein; and
(b) comparing the genotype of the genetic sample at each SNP in the set of SNPs to the genotype of a second genetic sample at each SNP in the set of SNPs to determine if the first and second genetic samples are the same or different.

Described herein are methods for determining whether a test genetic sample is genetically related to a selected cell. The methods include:
(a) obtaining a test genetic sample;
(b) analyzing the test genetic sample to determine the genotype of at least 10 SNPs selected from the group consisting of rs967968, rs718015, rs654559, rs723725, rs487616, rs1935571, rs2414908, rs1890035, rs554653, rs2254896, rs722152, rs1951096, rs953654, rs1157158, rs953183, rs2203657, rs2249248, rs1515561, rs1564935, rs1876054, rs1342947, rs2868931, rs1543193, rs951300, rs3847126, rs3847896, rs1986626, and rs1509577 to generate a test SNP pattern including the identity of the genotype of the at least 10 SNPs;
(c) comparing the test SNP pattern to a plurality of reference SNP patterns to identify the reference SNP pattern that matches the test SNP pattern, wherein each reference SNP pattern is associated with a selected reference genetic sample and comprises the identity of the genotype of the at least 10 SNPs for the associated genetic sample; and
(d) determining that the test genetic sample is genetically related to a reference genetic sample associated with the reference SNP pattern that matches the test SNP pattern at a predetermined number of SNPs, e.g., at least 60%, 70%, 80%, 90%, or 100% of the SNPs, in the test SNP pattern. A match with a higher percentage of SNPs will provide a result of identity with greater confidence. In some embodiments, the reference SNP pattern matches at least 8 SNPs in the test SNP pattern.

In some cases, the methods include analyzing the nucleic acid sample to determine the genotype no fewer than 20 polymorphic sites selected from the group consisting of rs967968, rs718015, rs654559, rs723725, rs487616, rs1935571, rs2414908, rs1890035, rs554653, rs2254896, rs722152, rs1951096, rs953654, rs1157158, rs953183, rs2203657, rs2249248, rs1515561, rs1564935, rs1876054, rs1342947, rs2868931, rs1543193, rs951300, rs3847126, rs3847896, rs1986626, and rs1509577.

In most cases, it will be desirable to determine that a test genetic sample and a reference genetic sample are likely to be identical if all of the genotype calls for the SNPs in the panel are identical.

In various embodiments, the test genetic sample is determined to be genetically related to the reference genetic sample associated with the reference SNP pattern that matches the test SNP at all of the SNPs in the test SNP pattern; at least one of reference genetic samples includes genetic material from an NCI-60 cell line; and/or the reference genetic samples include genetic material from at least 40 of the NCI-60 cell lines.

Also described herein are methods for identifying at least one single nucleotide polymorphism (SNPs) useful for distinguishing genetic samples. The methods include:
(a) obtaining a population of genetic samples;
(b) analyzing each genetic sample at each SNP of a plurality of SNPs to determine:
  i) $N'_{aa}$, the number of genetic samples in which the SNP is homozygous for a first allele,
  ii) $N'_{bb}$, the number of genetic samples in which the SNP is homozygous for a second allele, and
  iii) $N'_{ab}$, the number of genetic samples in which the SNP is heterozygous for a first and a second allele; and
(c) identifying a SNP where the ratio $N'_{aa}:N'_{bb}:N'_{ab}$ is approximately 1:1:2 as a SNP useful for distinguishing genetic samples.

Genetic material obtained from biological samples can be analyzed at the selected SNPs by any of a variety of methods. For example, pairs of PCR primers can be used to make allele calls at each of the selected SNPs. However, any method for genotyping SNPs can be used.

Because the methods described herein identify a relatively small number of SNPs that are useful for analyzing a group of biological samples, analysis of biological samples is rapid and cost effective. The number of SNPs analyzed is relatively small because the methods described herein are capable of identifying the SNPs that are most informative for a given set of biological samples.

The SNP panel identification assays (SPIAs) described herein can be used to solve a variety of problems, including, but not limited to: determining whether a given cell line is identical to another cell line; identifying identical samples in a set of patient samples; confirmation of the identity of passaged cell lines, confirmation of the identity of passaged xenografts; and matching normal and tumor cell samples from a single patient. Put simply, the methods and tools described herein can be used in any situation where it is necessary to identity a genetic sample. Thus, the methods described herein can be used to determine whether two test biological samples are the same or different. The methods described herein can be used to determine whether a test biological sample is identical to a reference biological sample. Thus, a set of biological samples can be analyzed to determine a genetic barcode for each sample, thereby creating a reference library of genetic barcodes. A test biological sample can be analyzed to produce a genetic bar code which can then be compared to a library of reference bar codes to identify the test biological sample.

In some cases a first, smaller SNP panel is used to analyze a sample or set of samples. If this first SNP panel proves to be adequate for sample identification, no further analysis need be conducted. However, if some of the results are ambiguous or if a higher degree of confidence is required, the samples can be analyzed with a larger SNP panel.

As explained in greater detail below, the analytical methods described herein were first applied to the analysis of NCI60 Cell Lines. These cell lines are very commonly used in cancer research. For example, The National Cancer Institute maintains a database of microarray expression data for NCI60 Cell Lines as well a database containing information on toxicity of approximately 70,000 compounds for cells of NCI60 cell lines. The analysis described below provides a means for identifying a relatively small number of SNPs that can be used to differentiate and identify cells of the NCI60 cell lines. This analysis revealed that MDA-MB435, which is identified as a breast cancer cell line is genotypically identical to the M14 melanoma cell line. In addition, at least two breast cancer cell lines among the NCI 60 Cell Lines exhibit genetic identity with the MCF-7 cell line. Such mis-identification, inadvertent cross-contamination or errors in sample identification can have a profoundly adverse effect on experimental results and their interpretation. For example, a search of the National Library of Medicine's PubMed database identified more that 400 publications that erroneously identify MDA-MB435 as a breast cancer cell line.

In another aspect, the present invention features a database comprising a plurality of records. Each record includes at least one, two or preferably all of the following: data on the identity of a number of SNPs, e.g., at least two, preferably at least three, four, or more SNPs, identified using a method described herein, and optionally a source identifier that indicates the cell, tissue, or subject from which the biological sample was taken.

Also included is a machine-readable medium that stores software implementing the methods described herein. As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media. A variety of data storage structures are available to a skilled artisan for creating a machine-readable medium having recorded thereon the data described herein. The choice of the data storage structure will generally be based on the means chosen to access the stored information. In addition, a variety of data processor programs and formats can be used to store the information of the present invention on computer readable medium.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 7A is a histogram showing the number of SNPs selected at each round. FIG. 7B is a histogram showing the heterozygous rate of each selected SNP evaluated on the test set. FIG. 7C shows the selection frequency of each SNP. The mean number of SNPs was 47.6 (std dev=8.1). The mean percentage of heterozygous SNPs in the test set was 0.374 (std dev=0.07). The total number of SNPs selected was 345.

FIG. 8A is a histogram showing the number of SNPs selected at each round. FIG. 8B is a histogram showing the heterozygous rate of each selected SNP evaluated on the test set. FIG. 8C shows the selection frequency of each SNP. The mean number of SNPs was 46.1 (std dev=6.4). The mean percentage of heterozygous SNPs in the test set was 0.33 (std dev=0.075). The total number of SNPs selected was 430.

FIG. 10 depicts the top 40 SNPs selected using equally weighted distribution.

FIG. 11 depicts the top 40 SNPs selected using Harvey-Weinberg equilibrium.

FIG. 14 is a table listing certain SNPs (identified by RefSNP ID ("rs_"; see the SNP database available on the internet at ncbi.nlm.nih.gov) useful for analyzing the cell samples analyzed in the study described herein together with the chromosome, the cytoband and alleles for each SNP. Also listed are one suitable right primer and two suitable left primers for assessing each SNP together with the expected product size for the amplification product. Primers listed on FIG. 14 (1-3) have SEQ ID NOs 1-84 respectively.

FIG. 15 is provides the flanking sequence, SEQ ID NOs 85-113 respectively, for each SNP listed in FIG. 14. The two alleles for each SNP are shown in brackets.

DETAILED DESCRIPTION

To identify a reasonable number of SNPs (indexes) such that $N_{SNP}$-nupla Calls$_{IND}$ is essentially unique for each sample it was first necessary to determine how many SNPs would be needed ($N_{SNP}$). This, of course, depends on the number of samples one wishes to distinguish. Most SNPs have two possible alleles (i.e., one of two possible nucleotides are present at the polymorphic position). Thus, there are three possible states (allele calls) for each SNP. If one of the two possible nucleotides at a given SNP is referred to as "A" and the other is referred to as "B," then there are three possible allele calls: AA, BB and AB. For simplicity in the formulas below, these genotypes are referred to as A, B and AB.

$N_{SNP}$ MIN, i.e., the minimum number of SNPs needed, depends on how many samples one aims to distinguish.

$$N_{sample} = N_{States}{}^{N_{SNP}}$$

$$N_{SNP} = \log_{N_{States}}(N_{Sample}) = \log_{N_{States}} 10 * \log_{10} N_{Sample}$$

$$N_{States} = 3, S = \{A, B, AB\}.$$

Figure 1:
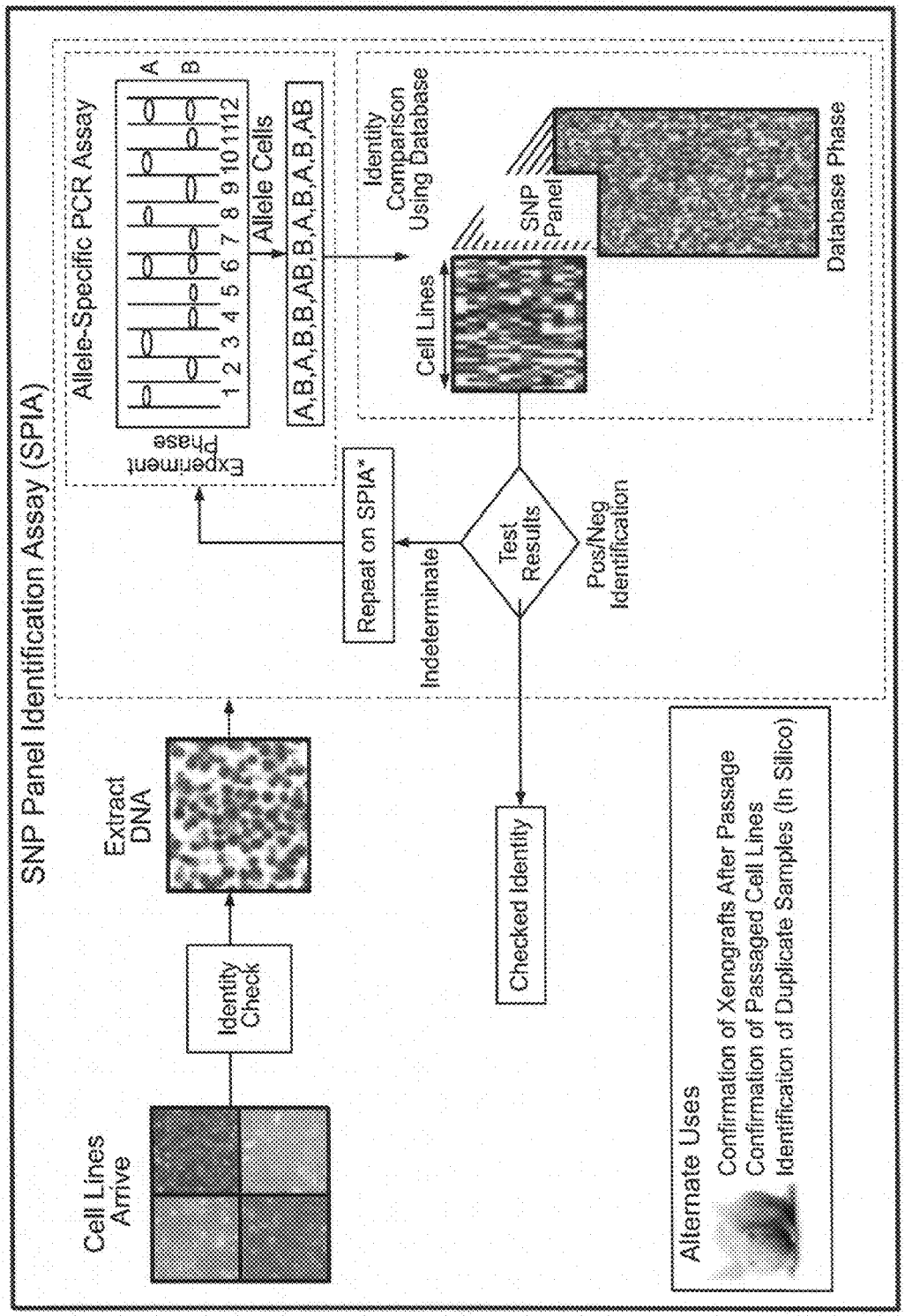
FIG. 1 is a schematic diagram depicting one example of how a panel of SNPs can be used to confirm the identity of a biological sample.
Figure 2:
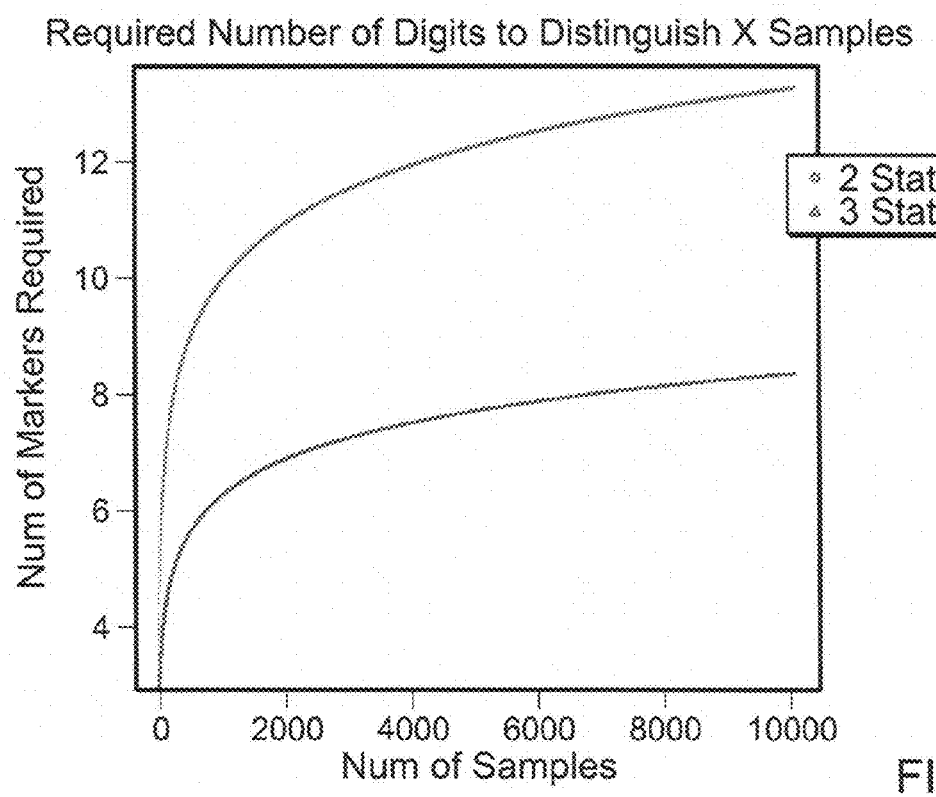
FIG. 2 is a line graph depicting the relationship between the minimum number of markers that must be analyzed to distinguish different samples and the number of samples to be distinguished. The red line depicts a situation in which each marker has two states, and the blue line depicts a situation in which each marker has three states.

The results of this calculation are shown in FIG. 2.

In some embodiments, the number of SNPs actually used in the analysis will not generally be a great as required for the highest level of certainty. Instead, the number of SNPs used will depend on the number which can be analyzed in an efficient manner and the degree of certainty required. However, the number of SNPs that should be analyzed will generally be somewhat larger than the theoretical minimum in order to take into account the occurrence of no calls and other vagaries of actual data Desirable SNPs are those that are highly variable across the population of samples one wishes to analyze, e.g., those which have minor allele frequency equal to about 0.5 and heterozygosity equal to about 0.5. Thus, a SNP that can be G or C, but is homozygous G (i.e., G/G) in 90% of the samples is not particularly useful. However, a SNP that can be C or G and is homozygous G in more than ⅓ of the samples and homozygous C in more than ⅓ of the samples is more useful.

At the outset two selection criteria were considered. The first criteria was based on an equally weighted distribution (EWD), where ⅓ of the calls are A, ⅓ of the calls are B, and ⅓ of the calls are AB, and there is a lower boundary on the call rate. This criteria optimizes the probability of having different calls. The second criteria is based on the Harvey-Weinberg equilibrium (HWE) where ¼ of the calls are A, ¼ of the calls are B, and ½ of the calls are AB, there are elastic boundaries, and there is a lower boundary on the call rate. This criteria respects expected biological distribution.

165 cell lines were selected to be analyzed using both techniques in order to determine which method yields more reliable results. The analysis was begun with this dataset of 165 cell lines. To eliminate pairs of cell lines that appeared to be duplicates, during the selection process of our SNP panel, the distance between all possible pairs of cell lines was evaluated using the Affymetrix, Inc. GeneChip® Human Mapping 50K Xba 240 array, which permits analysis of 50,000 SNPs.

A similarity measure was used to evaluate the distance between samples for identity measurements. The distance metric for this analysis is proportional to the number of mismatches. It is defined as:

$$D(CL1, CL2) = \frac{1}{vN_{SNPs}} \sum_{i=1...N_{SNPs}} d(cl1_i, cl2_i), \text{ where}$$

$$d(cl1_i, cl2_i) = \begin{cases} 1 \text{ if } cl1_i \neq cl2_i \\ 0 \text{ if } cl1_i = cl2_i \text{ or } cl_i = NoCall, \end{cases}$$

$N_{SNPs}$ is the number of SNPs you are considering, and $$vN_{SNPs} = Card(T), T = \{i : cl1_i \neq NoCall \cap cl2_i \neq NoCall\}.$$

Therefore: $vN_{SNPs} \leq N_{SNPs}$.

Different weights can be included for different type of mismatches:

$$d(cl1_i, cl2_i) = \begin{cases} w_{ErType} * 1 \text{ if } cl1_i \neq cl2_i \\ 0 \text{ if } cl1_i = cl2_i \end{cases}$$

Figure 3:
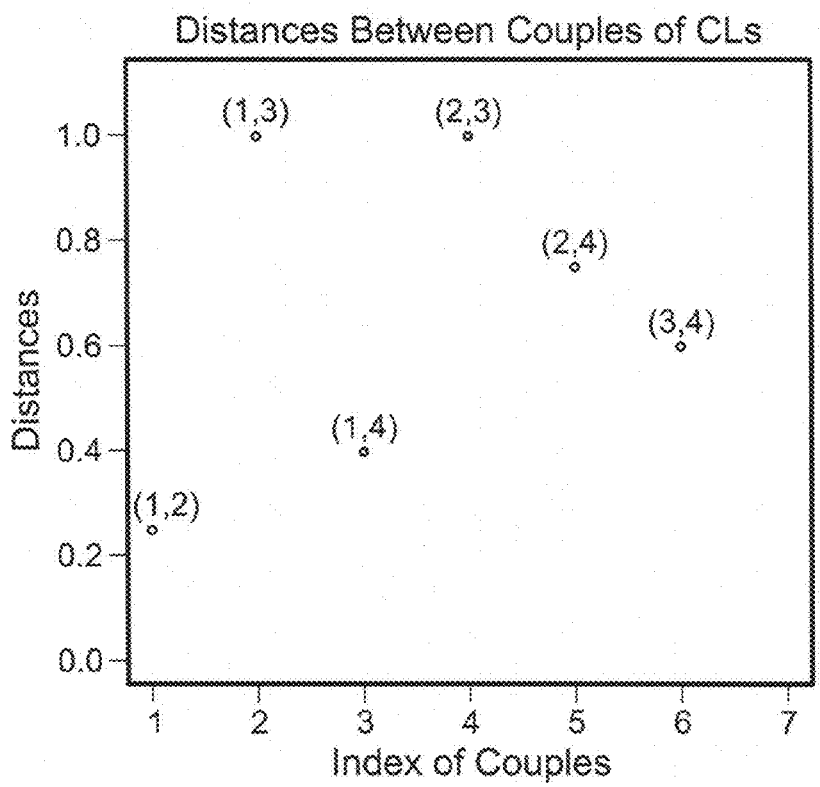
FIG. 3 is a dot graph depicting a simple example of the distance measure for four samples (S1, S2, S3 and S4) with five SNPs (each of which can have one of three genotypes: A, B or AB). $N_{SNPs}=5$; S1=(A, A, A, A, A); S2=(A, A, A, NoCall, B); S3=(B, B, AB, AB, AB); S4=(B, B, A, A, A); $vN_{SNPs}=5$, unless distances are measured with respect to S2 ($vN_{SNPs}=4$).

Every mismatch counts 1, every match counts 0, and the distance is normalized over the number of available calls for each pair of samples. Min Distance=0, Max distance=1. FIG. 3 shows a simple example of the distance measure for four samples (S1, S2, S3 and S4) for five SNPs (each of which can be A, B or AB).

The implemented distance function returns: D, $vN_{SNPs}$, $N_{SNPs}$, number of SNPs with one NoCall, number of SNPs with both NoCall, number of mismatches of different homozygosity (A vs B or viceversa), number of mismatches of type homozygosity vs heterozygosity (all combinations), number of homozygous matches and number of heterozygous matches. The expected distance D of two random samples, accordingly to the Hardy-Weinberg equilibrium, is 0.625. In fact, for unrelated samples we can write the joint probabilities as shown below. This is where the joint probability of two events E1 and E2, P(E1,E2) or P(E1 AND E2) is P(E1,E2)=P(E1)*P(E2|E1) and P(E2|E1) is called the conditional probability of E2 given E1.

$$P(A,A) = P(A) * P(A|A) = P(A) * P(A) = 0.0625$$

$$P(B,B) = P(B) * P(B|B) = P(B) * P(B) = 0.0625$$

$$P(AB,AB) = P(AB) * P(AB|AB) = P(AB) * P(AB) = 0.25$$

The match probability P_pm is P(A,A)+P(B,B)+P(AB,AB).

The mismatch probability P_mm is: P_mm=1−P_pm=1−0.375=0.625.

This similarity analysis identified several pairs of cell lines that were very close to each other. All of these pairs are listed in TABLE 1. Some, the positive controls, were already known to be very similar or identical. Other pairs were not expected to be so similar or identical.

TABLE 1

| Name CL1 | Name CL2 | Dist | Entries | | NA | | Diff | | equal | |
| | | | Valid | total | OneNA | BothNA | Ho-Ho | Ho-Het | Ho-Ho | Het-Het |
|---|---|---|---|---|---|---|---|---|---|---|
| M_14 | MDA.MB435 | 0.025 | 44620 | 58633 | 10525 | 3488 | 8 | 1132 | 37881 | 5599 |
| MCF7(*) | BT.20 | 0.022 | 44457 | 58633 | 10422 | 3754 | 4 | 981 | 39067 | 4405 |
| MCF7 | X25X_KPL.1 | 0.022 | 44040 | 58633 | 10963 | 3630 | 3 | 979 | 38530 | 4528 |
| BT.20 | X25X_KPL.1 | 0.023 | 46791 | 58633 | 9423 | 2419 | 5 | 1117 | 40658 | 5011 |
| NCI.ADR.RES | OVCAR.8 | 0.006 | 49200 | 58633 | 5846 | 3587 | 0 | 327 | 44975 | 3898 |
| NCI.H460 | H2195 | 0.036 | 39809 | 58633 | 14715 | 4109 | 1 | 1446 | 34585 | 3777 |
| SNB.19(**) | U251 | 0.028 | 48940 | 58633 | 7367 | 2326 | 0 | 1394 | 43044 | 4502 |
| X37X_184A1(***) | X35X_184B5 | 0.091 | 56513 | 58633 | 1914 | 206 | 282 | 4891 | 40084 | 11256 |
| H1450 (****) | H2141 | 0.005 | 47077 | 58633 | 8087 | 3469 | 0 | 240 | 42473 | 4364 |
| H1450 | H220 | 2E−05 | 48048 | 58633 | 6024 | 4561 | 0 | 1 | 42496 | 5551 |
| H2141 | H220 | 0.005 | 46518 | 58633 | 8399 | 3716 | 1 | 229 | 41878 | 4410 |

Figure 4:
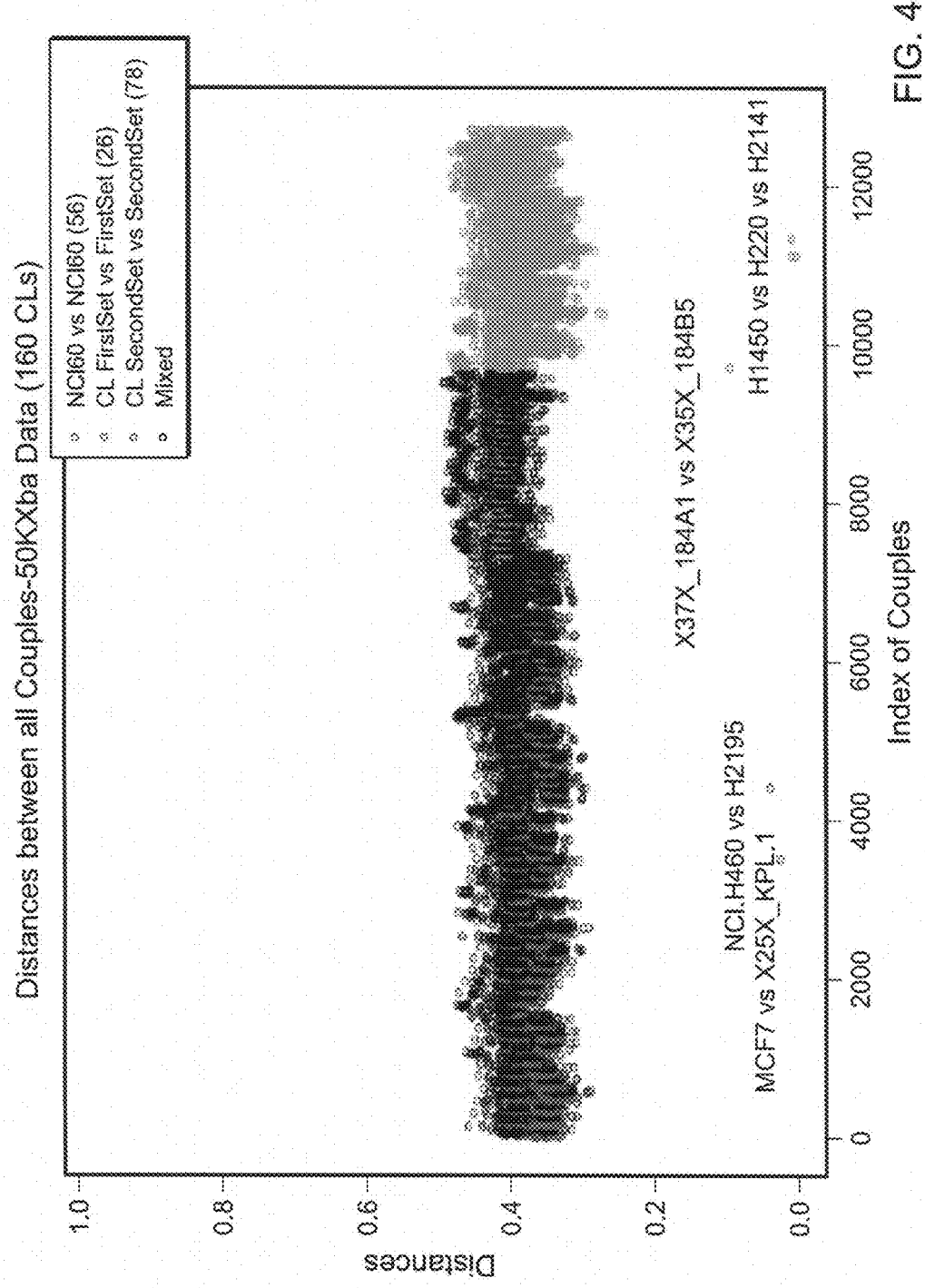
FIG. 4 is a graphical representation of the distance between all pairs of the 165 cell lines analyzed, excluding the cell lines in Table 1.

FIG. 4 is a graphical representation of the distance between all pairs excluding the cell lines in Table 1. Eliminating all cell lines having a distance, D, less than 0.2, left 155 cell lines with average distance of 0.383 (median=0.385, min=0.26 and max=0.48).

Next a subset of the 50,000 SNPs present in the Gene-Chip® Human Mapping 50K Xba 240 Array (Affymetrix, Inc.) was identified for use in further analysis. Although a variety of selection criteria are reasonable, those SNPs were used that: 1) had an assigned RS number in the NCBI SNP database; 2) were present in the Affymetrix, Inc. GeneChip Mapping 10K Array; and 3) were not located in an intron. This lead to the selection of about 5,300 SNPs that would be analyzed in the 155 selected cell lines.

Figure 5:
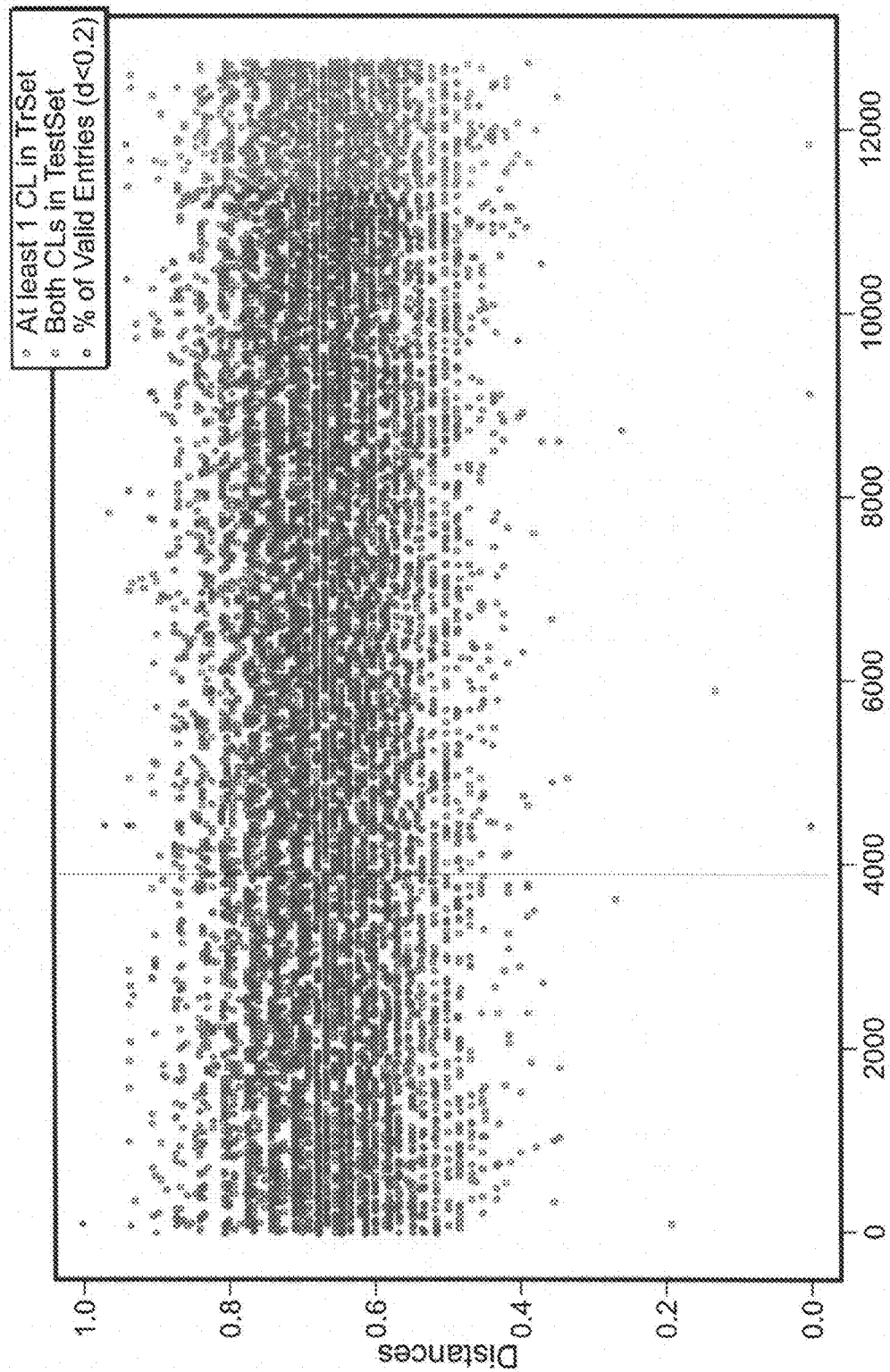
FIG. 5 shows the pair distance plotted as a function of pair index for the equally distributed call selection criteria using 31 SNPs. In this figure, the red dots indicate that both cells lines of the pair were part of the test set.
Figure 6:
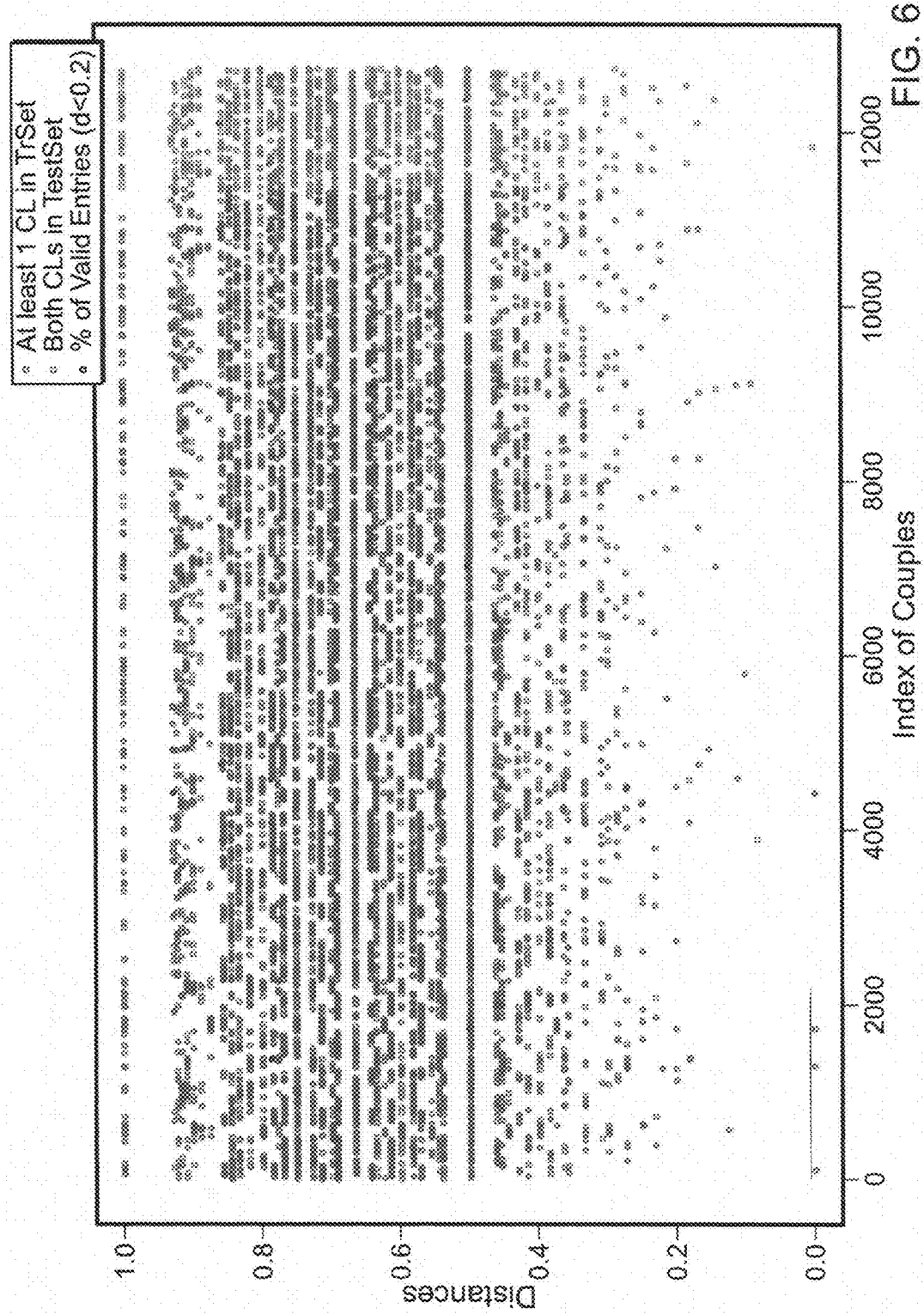
FIG. 6 shows the pair distance plotted as a function of pair index for the Harvey-Weinberg equilibrium call selection criteria using 14 SNPs. In this figure, the red dots indicate that both cells lines of the pair were part of the test set.

The dataset of 155 cell lines was divided into a training set (about ⅔ of the cell lines) and a test set (about ⅓ of the cell lines) and the two potential selection criteria (equally distributed calls and Harvey-Weinberg equilibrium) were applied separately for a small subset of SNPs. FIG. 5 shows the pair distance plotted as a function of pair index for the equally distributed call selection criteria using 31 SNPs, and FIG. 6 shows the pair distance plotted as a function of pair index for the Harvey-Weinberg equilibrium call selection criteria using 14 SNPs. In these figures the red dots indicate that both cells lines of the pair were part of the test set.

Next, the two selection criteria were analyzed in order to answer the following questions: 1) How stable is the selection criteria with respect to different training sets?; and 2) Given a certain number of samples and a confidence level, how can the proper cutoff for the distance measure be determined?

Stability of the Selection Criteria with Respect to Different Training Data Sets A bootstrap analysis was run on the training data set for 100 rounds and at each round the unselected cell lines create the test set. At each round 100 cell lines were randomly selected, the selection criteria (EDC or HWE) was applied without any constraint on the number of SNPs, the selection equilibrium was verified on the test set, and the selected SNPs were stored. The selection of the SNPs for use in SPIA was based on two factors. First, the SNPs should be frequently selected in different runs (e.g., a selection rate of at least 40%). Second, the SNPs should be distributed across the genome.

Figure 7A:
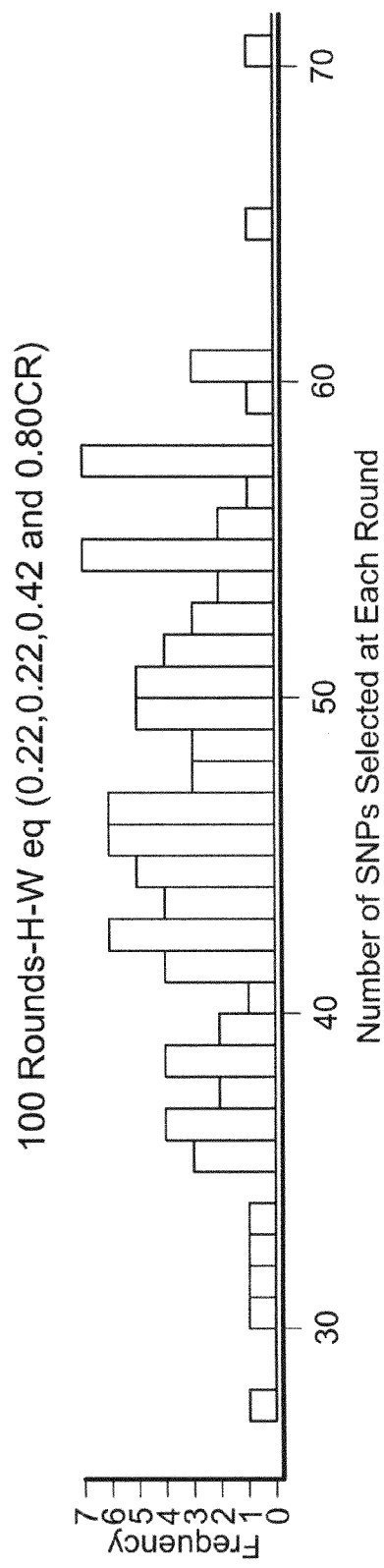
FIGS. 7A-7C depict the results of analysis using Harvey-Weinberg equilibrium selection criteria (A=0.22, B=0.22, and AB=0.42 and the call rate is at least 0.8).
Figure 7B:
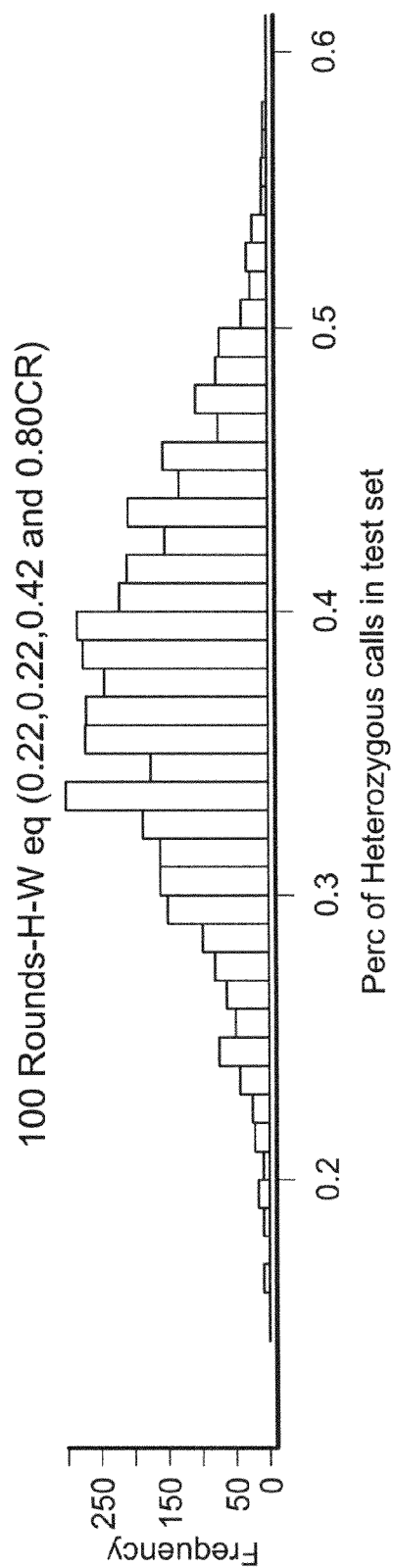
Figure 7C:
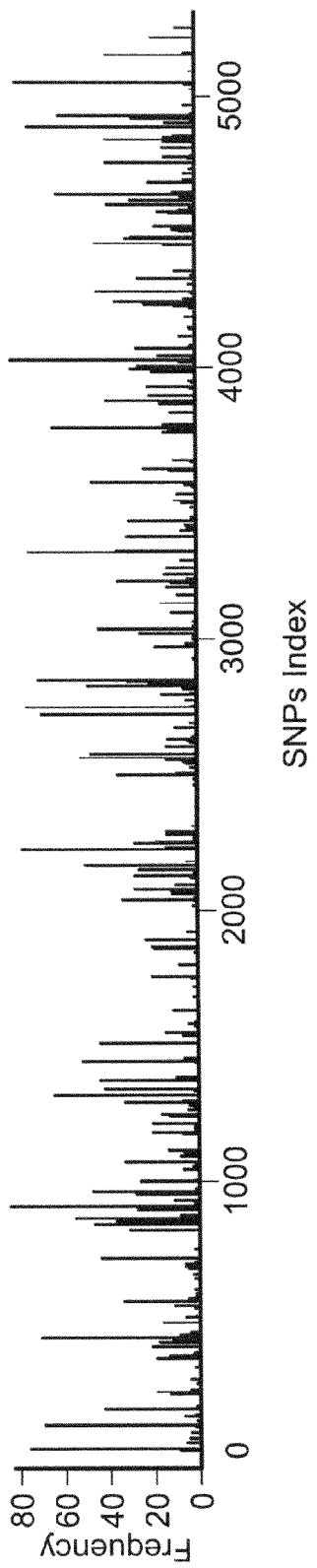

FIGS. 7A-7C depict the results of this analysis for the HWE selection criteria (A=0.22, B=0.22, and AB=0.42 and the call rate is at least 0.8). FIG. 7A is a histogram showing the number of SNPs selected at each round. FIG. 7B is a histogram showing the heterozygous rate of each selected SNP evaluated on the test set. FIG. 7C shows the selection frequency of each SNP. The mean number of SNPs was 47.6 (std dev=8.1). The mean percentage of heterozygous in the test set was 0.374 (std dev=0.07). The total number of SNPs selected was 345.

Figure 8A:
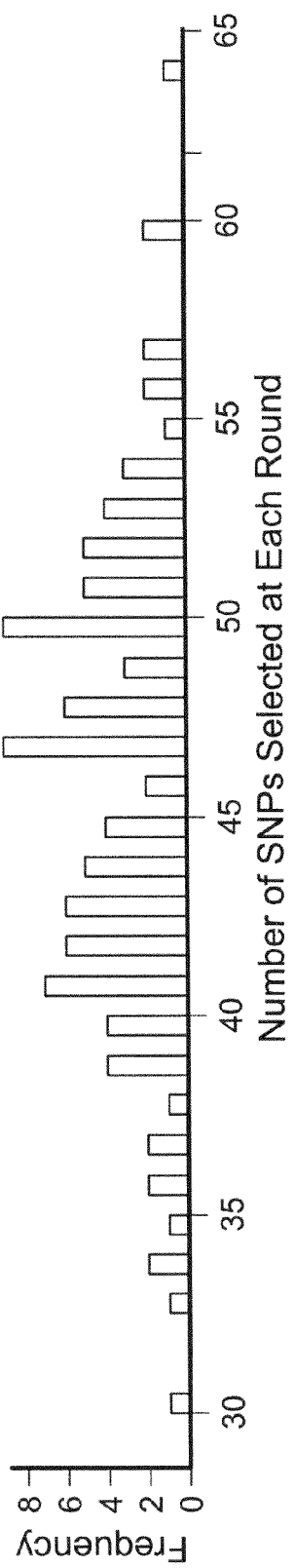
FIGS. 8A-8C depict the results of this analysis for the equally weighted distribution criteria selection criteria (A=0.33, B=0.33, AB=0.33, call rate is at least 0.9, and minimum frequency is 30).
Figure 8B:
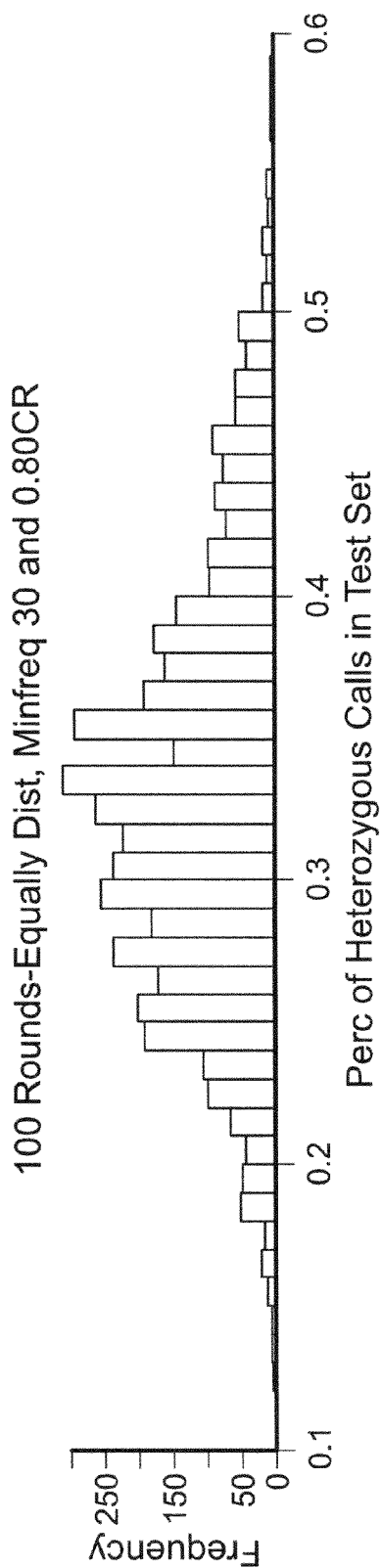
Figure 8C:
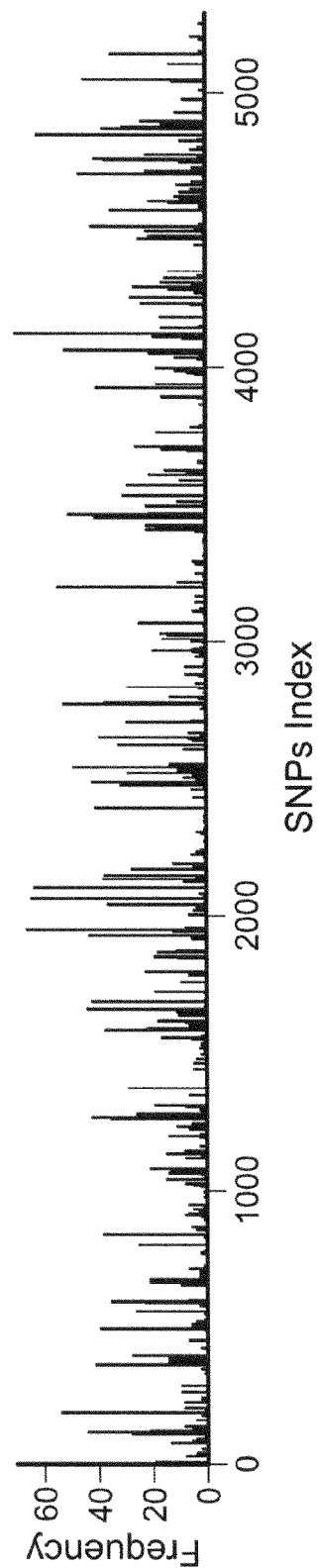

FIGS. 8A-8C depicts the results of this analysis for the EWD selection criteria (A=0.33, B=0.33, AB=0.33, call rate is at least 0.9, and minimum frequency is 30). FIG. 8A is a histogram showing the number of SNPs selected at each round. FIG. 8B is a histogram showing the heterozygous rate of each selected SNP evaluated on the test set. FIG. 8C shows the selection frequency of each SNP. The mean number of SNPs was 46.1 (std dev=6.4). The mean percentage of heterozygous in the test set was 0.33 (std dev=0.075). The total number of SNPs selected was 430.

Comparing the HWE selection criteria and EWD criteria, it appears that the HWE criteria provides more stable results with respect to variations in the training set. The heterozygous call rate is well conserved in the test set whether the HWE criteria or the EWD criteria is used. However, when the heterozygous call rates evaluated on the test set are compared with the heterozygous call rates for Caucasian samples reported by Affmetrix, Inc., it appeared that samples from Caucasians are not well represented. When the SNPs selected using each criteria are ranked by selection rate and the 40 highest ranked SNPs are selected, the mean selection rate was 0.44 (std dev=0.09) for the EWD selection criteria and 0.55 (std dev=0.14) for the HWE selection criteria.

While it is desirable to select the SNPs with a highest selection rate, there are a number of other factors that should be taken into account when selecting a set of SNPs for identifying or comparing/distinguishing cells. For example: the heterozygosity rate is desirably similar for different population (African American, Asian, Caucasian); the SNPs are desirably in regions that are not commonly deleted; the SNPs are desirably within exons; the SNPs are preferably distributed across a plurality of chromosomes (e.g., across all chromosomes).

Figure 9A:
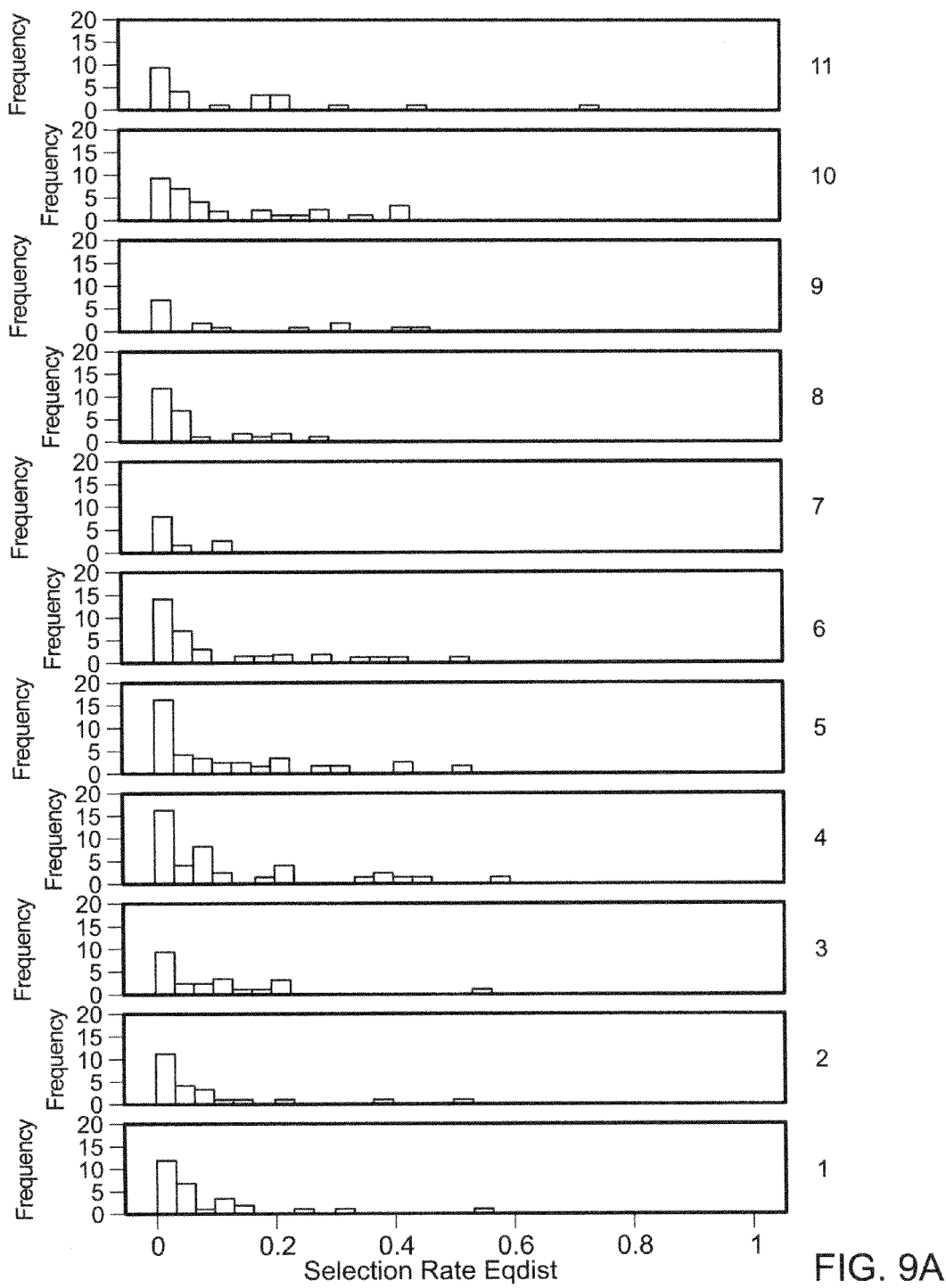
FIGS. 9A-9D are histograms of selection rates stratified on each of the chromosomes for the SNPs selected using equally weighted distribution (9A-9B) and Harvey-Weinberg equilibrium (9C-9D).
Figure 9B:
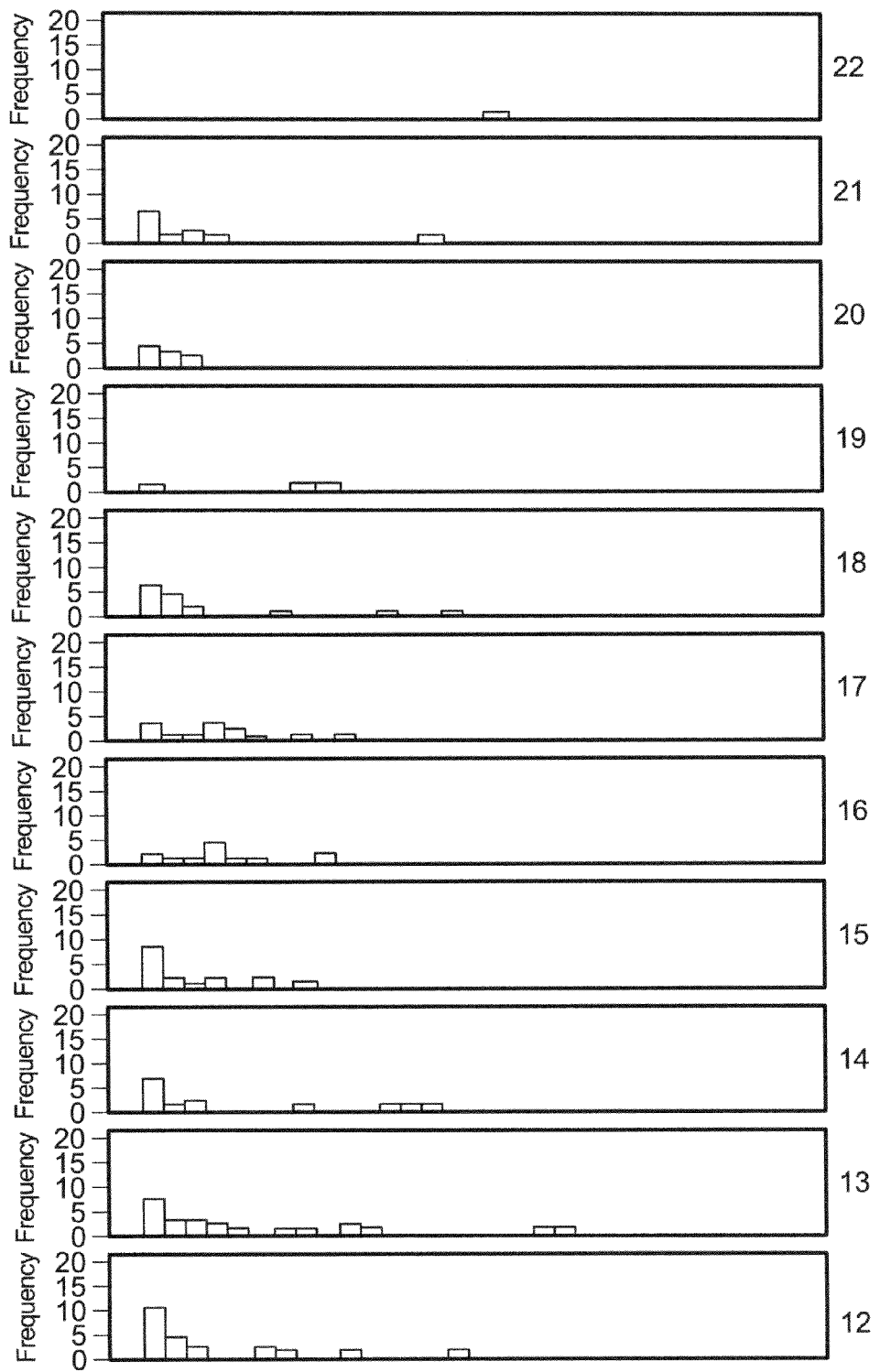
Figure 9C:
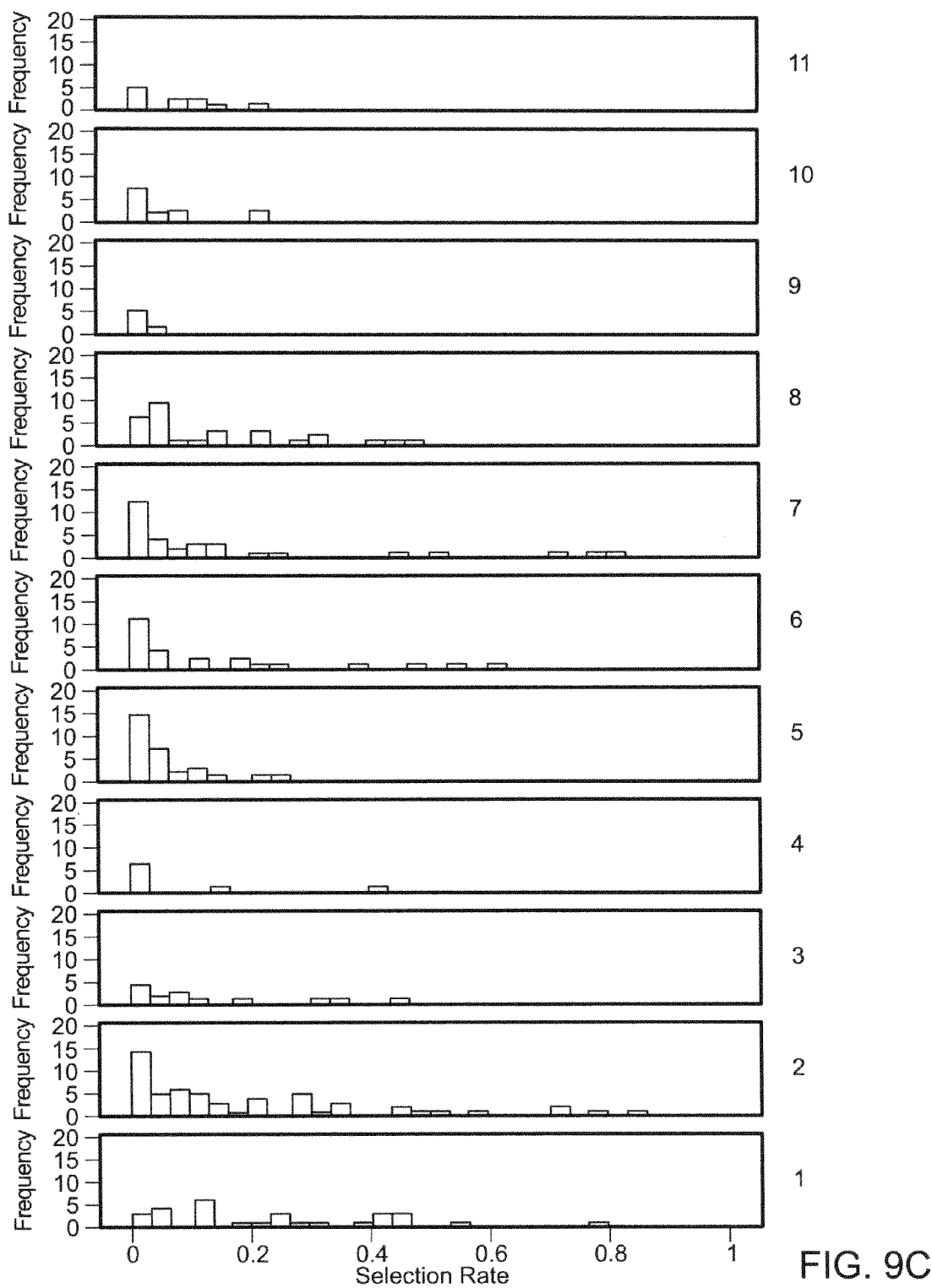
Figure 9D:
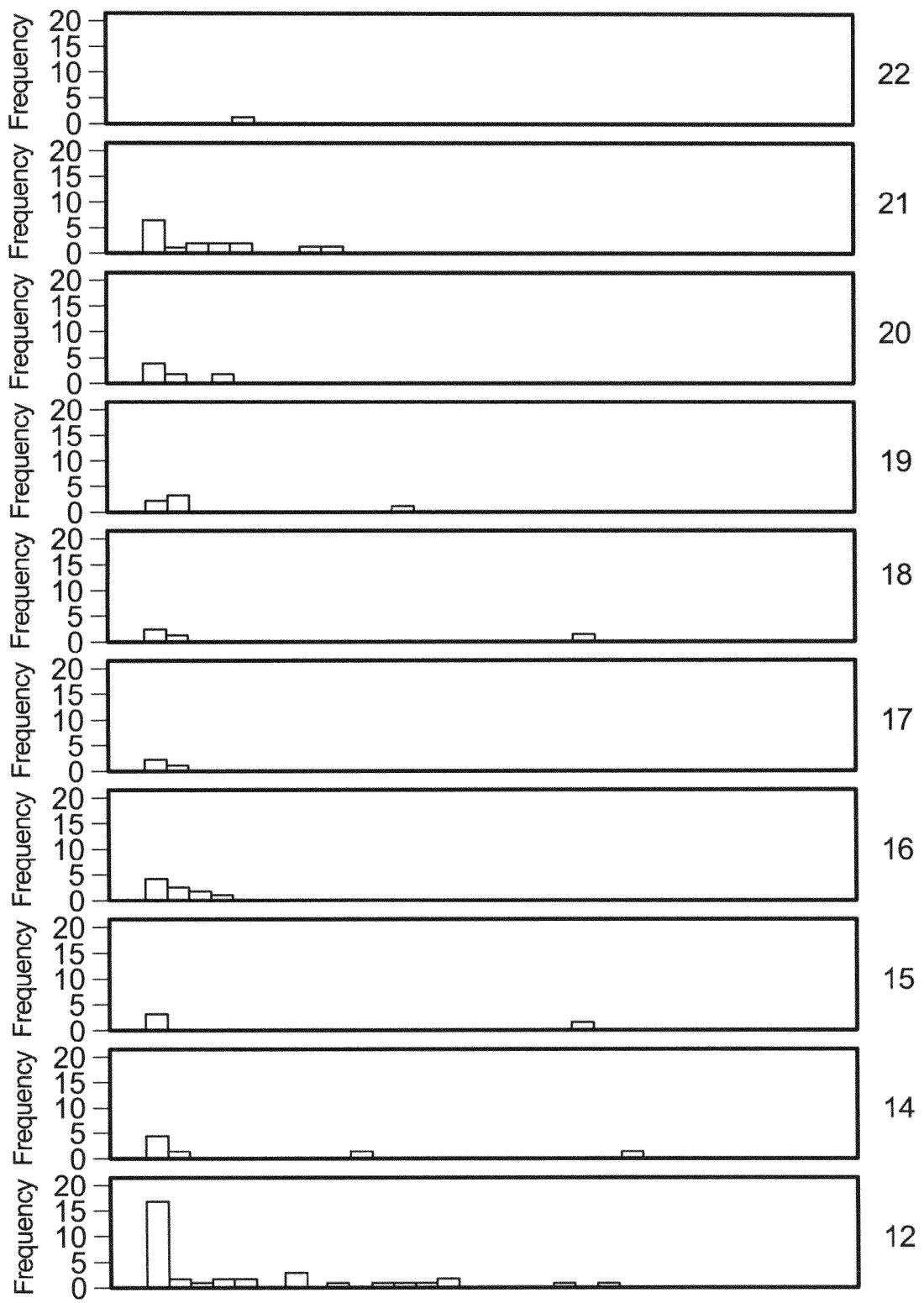

FIGS. 9A and 9B are histograms of selection rates stratified on chromosomes for the SNPs selected with EWD and HWE respectively. FIGS. 10 and 11 are the top 40 SNPs selected with EWD and HWD, respectively.

Determining Cut-off for the Distance Measure

A cut-off distance measure must be used when comparing the genotype analysis for two samples at the various selected SNPS. This cut-off is the distance measure below which it cannot be stated that two samples are not the same sample.

The distance of two test samples can be compared with the distance expected for two true paired samples. More precisely, it can be determined whether the distance between two test samples is within the distribution of distances of a population of true paired samples. Provided that the confidence limit needed is defined, if the distance between two test samples is not within the distribution of distances of a population of true paired samples, it can be determined with confidence that the two test samples are not paired and, of course, not the same sample. This approach includes the test against being exactly the same sample. Where the test result is uncertain, a second set of SNPs can be run.

To apply the test an estimate of the mis-match probability (or match probability) of true paired samples and the experimental error rate must be used, so that the distance distribution can be determined.

For each pair of samples distance D was evaluated, and, based on number of SNPs used ($vN_{SNPs}$), the probability of getting the same distance for two true paired samples is tested. It is assumed that the SNPs (SNPs calls) are independent, i.e., the call at locus i does not depend on call at locus i-1. The probability of having k matches (successes) out of N SNPs (runs) follows the a binomial distribution:

$$p_k = \binom{N}{k} p^k q^{N-k} = \frac{N!}{k!(N-k)!} p^k q^{N-k},$$

where p=P_pm and q=P_mm are the probability of success (match) and non-success (mismatch) respectively.

Given N, the sum over all possible k is equal to $$1 \left( \sum_{k=0}^{N} p_k = 1 \right).$$

A property of binomial distribution is that after many runs, the binomial distribution approximates the Gaussian distribution. That is useful in evaluating the probabilities. After many runs, the mean number of successes $k_{mean}$ is $k_{mean}$=Np and Sd_$k_{mean}$=sqrt(Np(1-p)). For a normal distribution, the probability that a measurement falls within n standard deviations of the mean (i.e., within the interval [$k_{mean}$-n sd, $k_{mean}$+n sd]) is given by the integral of the distribution function. Given two samples, the probability of matched (P_pm) and of mismatched (P_mm) calls at each SNP locus is known (or can be evaluated from data). The sum of the probability of match and mismatch for each SNP locus is always equal to 1: P_pm+P_mm=1.

The joint probability of two events E1 and E2, P(E1, E2) or P(E1 AND E2) is P(E1,E2)=P(E1)×P(E2|E1) and P(E2|E1) is called the conditional probability of E2 given E1. Thus, the joint probability here is the sum, P_pm, of the homozygous joint probabilities (i.e., P(A,A) and P(B,B)) and of the heterozygous joint probability: P_pm=P(A,A)+P(B,B)+P(AB, AB).

For paired samples, such as normal and tumor samples from the same patient: P_mm(Norm,Tum)=P(A,B)+P(B,A)+P(A,AB)+P(B,AB)+P(AB,A)+P(AB,B)   P(A,B)=P(A)*P(B|A) and P(B,A)=P(B)*P(A|B) accounts for probability of double mutations; P(A,AB) and P(B,AB) are related to gain of heterozygosity; P(AB,A) and P(AB,B) are related to loss of heterozygosity.

Figure 12:
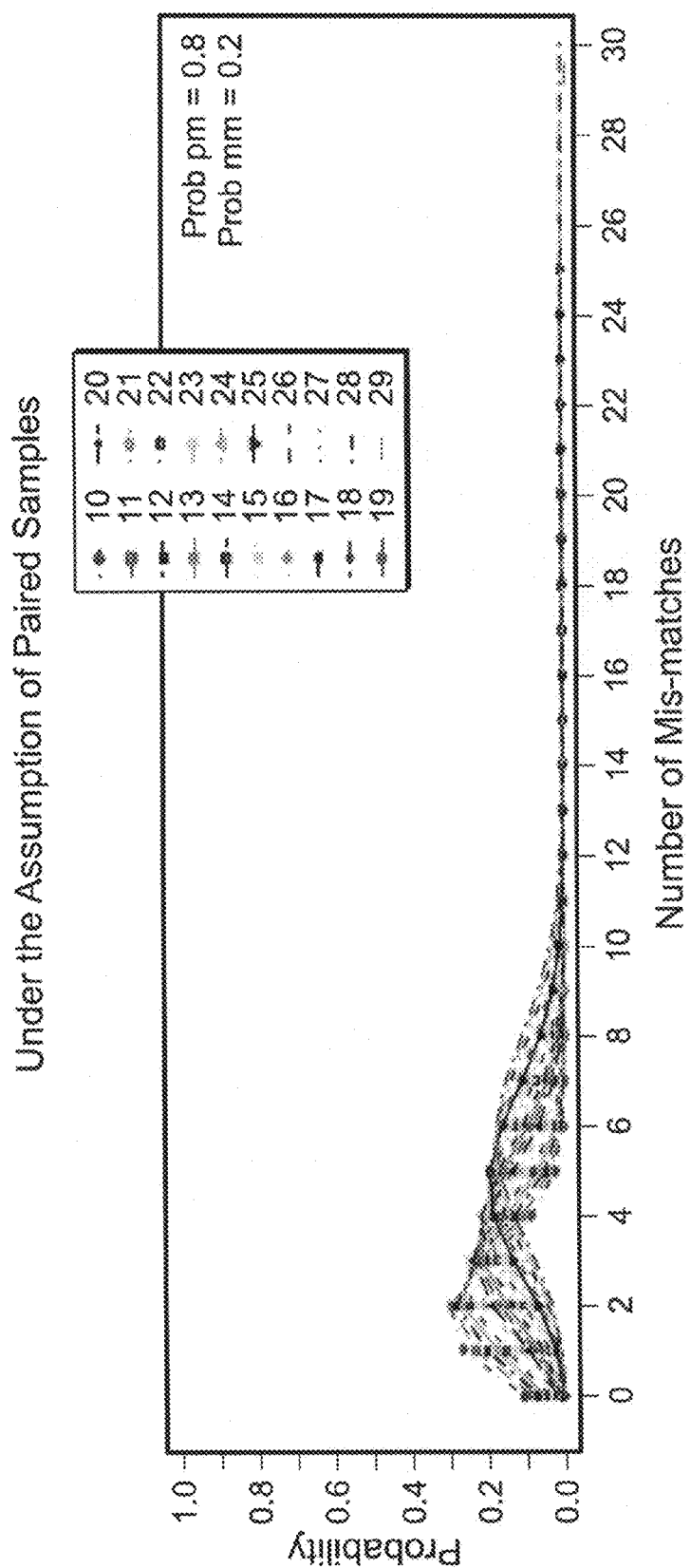
FIG. 12 depicts the probability distribution of being a pair versus the number of mismatches assuming that the mismatch probability is 0.2. Distributions for different $vN_{SNPs}$ are reported. Green dots identify distances which did not pass the test (confidence 95%; p_mm=0.2).
Figure 13:
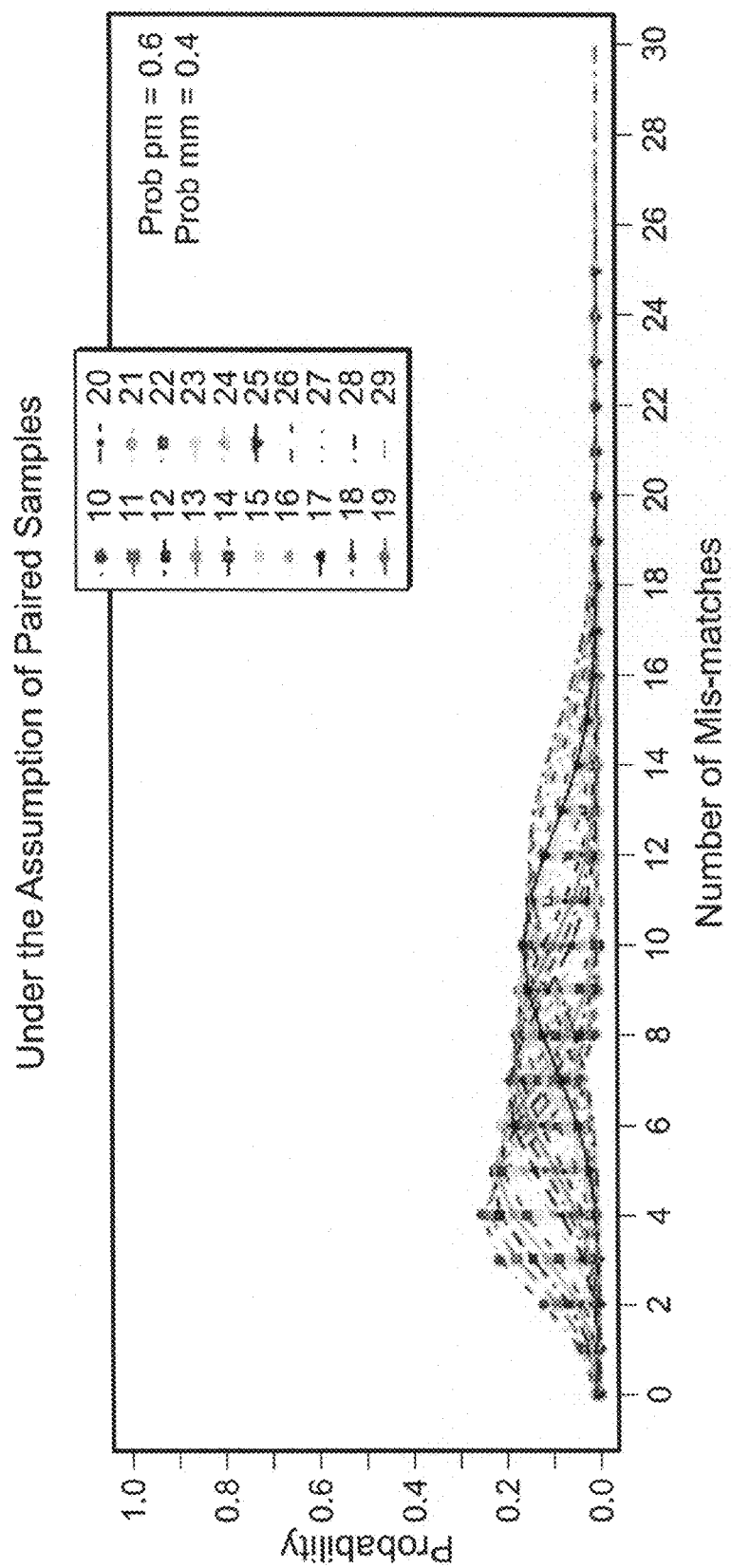
FIG. 13 depicts the probability distribution of being a pair versus the number of mismatches assuming that the mismatch probability is 0.4. Distributions for different $vN_{SNPs}$ are reported. Green dots identify distances which did not pass the test (confidence 95%; p_mm=0.2).

FIGS. 12 and 13 show the probability distribution of being a pair versus the number of mismatches, assuming that the mis-match probability is 0.2 and 0.4, respectively. Distributions for different $vN_{SNPs}$ are reported. Green dots in the two last scatter plots identifies distances which did not passed the test (confidence 95%; p_mm=0.2).

FIGS. 14 and 15 depict certain SNPs that were selected using the studies described above. These SNPs are particularly useful for analyzing NCI60 cells lines.

Analysis of Samples

The nucleic acids analyzed can be genomic DNA, cDNA, mitochondrial DNA, or any other source of nucleic acid. The nucleic acid can be amplified using any suitable method, including PCR, ligase chain reaction, transcription amplification, and self-sustained sequence replication. The nucleic acid can be obtained from any of a variety of biological samples, e.g., tissue, body fluid (e.g., blood, peritoneal fluid, spinal fluid and pleural fluid) and cells. Biological samples can also include sections of tissues, such as formalin-fixed sections or frozen sections. Cultured cells can also be analyzed.

SNPs can be genotyped using any convenient methods. For example, GeneChip® arrays from Affmetrix, Inc. are capable of analyzing 500,000 different SNPs using arrays of hybridization probes with a reported accuracy of 99.6% for homozygous calls and 96.3% for heterozygous calls. The technique is described in Genome Res 11:1913 (2001) and Human Muta 19:402 (2002). While standard GeneChip® arrays are useful for analyzing many SNPs, custom arrays can be designed to analyzed any SNP or group of SNPs. SNPs can also be genotyped using allele-specific PCR using primers that include sequence tags.

U.S. Pat. No. 6,709,816 (Affymetrix, Inc.) describes a high-throughput method for analyzing SNPs to determine if the sample is homozygous for a first allele, homozygous for a second allele or heterozygous at a give SNP. As explained in U.S. Pat. No. 6,709,816, SNPs can be accurately analyzed specificity by hybridizing uniquely tagged allele-specific nucleic acid sequences to corresponding tag probes in an array. Briefly, a nucleic acid sample is amplified using an allele-specific amplification such that uniquely tagged nucleic acids corresponding to different alleles of a polymorphic locus are generated. Nucleic acids corresponding to different alleles are linked to different tags. Each tag includes a sequence that is identical to all or part of a probe on a detection array. The method includes four steps: allele-specific amplification, labeling, hybridization, and detection. The allele-specific amplification employs allele-specific primers, each of which has an allele-specific 3' portion and a 5' portion that acts as a tag. The amplification products for each allele are labeled and hybridized to a solid support bearing appropriate probes in an array. Each probe in the array comprises the same or nearly the same sequence as the tag of an allele-specific primer.

The sequence tag is identical or nearly identical to the sequence of all or a portion of a respective probe in an array so as to allow specific binding between the complement of the tag and the probe. The sequence tags are selected so that they have similar hybridization characteristics and minimal cross-hybridization to other sequence tags.

Each pair of primers is designed to specifically amplify one allelic form of a polymorphic locus. The two primers in a pair of primers are complementary to opposite stands of the DNA region to be amplified. The first primer of the pair has a 3' nucleotide which is complementary to a specific allelic form of the SNP but not complementary to other allelic form (or forms). The first primer includes a portion at its 3' end which is complementary to the region of double stranded DNA to be amplified. The first primer also includes a portion at its 5' end which is a tag. The tag has the same sequence as all or a portion of a probe on a solid support. The tag sequence is not complementary to any significant portion of the DNA being amplified. The second primer can include a tag or not. The two primers hybridize to a double stranded nucleic acid at position that are less than 1,000 (100 or even 10) bases apart. The amplification generates a first amplified strand and a second amplified strand. The first strand includes a portion identical to all or part of the probe on the solid support and the second strand comprises a 5' portion complementary to all or part of the probe.

The amplified DNA is labeled before it is hybridized to a probe on a solid support. The amplified DNA is hybridized to probes which are immobilized to known locations on a solid support, e.g., in an array, microarray, high density array, beads or microtiter dish. The presence of labeled amplified DNA products hybridized to the solid support indicates that the nucleic acid sample contains at the polymorphic locus a nucleotide which is the same as the 3' terminal nucleotide of the first primer. The quantities of the label at distinct locations on the solid support can be compared, and the genotype can be determined for the sample from which the DNA was obtained.

Two or more pairs of primers can be used for determining the genotype of a sample. Each pair of primers specifically amplifies a different allele possible at a given SNP.

The hybridized nucleic acids can be detected, e.g., by detecting one or more labels attached to the target nucleic acids. The labels can be incorporated by any convenient means. For example, a label can be incorporated by labeling the amplified DNA product using a terminal transferase and a fluorescently labeled nucleotide. Useful detectable labels include labels that can be detected by spectroscopic, photochemical, biochemical, immunochemical, electrical, optical, or chemical means. Radioactive labels can be detected using photographic film or scintillation counters. Fluorescent labels can be detected using a photodetector.

Implementation

The methods, equations and algorithms described herein can be easily implemented in hardware or software, or a combination of both. The methods can be implemented in computer programs using standard programming techniques following the steps, algorithms, equations, and figures disclosed herein. The programs can be designed to execute on programmable processors or computers, e.g., microcomputers, each including at least one processor, at least one data storage system (including volatile and non-volatile memory and/or storage elements), at least one input device, such as a keyboard or push button array, and at least one output device, such as a monitor, e.g., a CRT or LCD monitor, or a printer. Program code is applied to input data to perform the functions described herein. The output information is applied to one or more output devices such as a printer, or a monitor, or a web page on a computer monitor with access to a website, e.g., for remote monitoring.

Each program used in the new system is preferably implemented in a high level procedural or object oriented programming language to communicate with a computer system. However, the programs can be implemented in assembly or machine language, if desired. In any case, the language can be a compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The system can also be considered to be implemented as a machine or computer-readable storage medium, configured with a computer program, where the storage medium so configured causes a computer to operate in a specific and predefined manner to perform the functions described herein.

Although any communications network can be used to obtain results from remote monitoring, the Internet or wireless systems provide useful choices to transmit data.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying at least one single nucleotide polymorphism (SNP) useful for analyzing a genetic sample, the method comprising:
   (a) obtaining a population of selected genetic samples;
   (b) separating the population of genetic samples into a first subpopulation of genetic samples comprising a portion of the genetic samples and a second subpopulation comprising the remaining genetic samples;
   (c) analyzing the genotype at each SNP of a plurality of SNPs for each genetic sample in the first subpopulation of genetic samples to determine for each SNP analyzed:
      i) $N_{aa}$, the number of genetic samples in which the SNP is homozygous for a first allele,
      ii) $N_{bb}$, the number of genetic samples in which the SNP is homozygous for a second allele, and
      iii) $N_{ab}$, the number of genetic samples in which the SNP is heterozygous for a first and a second allele;
   (d) for the genetic samples in the first subpopulation, ranking each SNP of the plurality of SNPs by how nearly the ratio $N_{aa}:N_{bb}:N_{ab}$ matches the ratio 1:1:2 to provide a ranking of SNPs;
   (e) analyzing the genotype at each SNP in the plurality of SNPs for each genetic sample in the second subpopulation of genetic samples to determine for each SNP:
      i) $N'_{aa}$, the number of genetic samples in which the SNP is homozygous for a first allele,
      ii) $N'_{bb}$, the number of genetic samples in which the SNP is homozygous for a second allele, and
      iii) $N'_{ab}$, the number of genetic samples in which the SNP is heterozygous for a first and a second allele;
   (f) for the genetic samples in the second subpopulation, determining how closely the ratio $N'_{aa}:N'_{bb}:N'_{ab}$ matches the ratio 1:1:2 to provide a score for each SNP;
   (g) designating a SNP that both ranks above a pre-determined cut-off in the ranking when analyzed in the first subpopulation and has a score above a pre-determined score when analyzed in the second subpopulation as a candidate SNP;
   (h) repeating steps (b)-(g) at least two times, each time designating one or more SNPs as a candidate SNP to generate at least two groups of candidate SNPs; and
   (i) identifying a SNP designated as a candidate SNP at least two times as a SNP useful for analyzing a genetic sample.

2. The method of claim 1, wherein steps (b)-(g) are repeated at least 10 times and wherein a SNP designated as a candidate SNP at least 4 times is identified as a SNP useful for analyzing genetic samples.

3. The method of claim 1, wherein steps (b)-(g) are repeated at least 100 times and wherein a SNP designated as a candidate SNP at least 40 times is identified as a SNP useful for analyzing genetic samples.

4. The method of claim 1, wherein steps (b)-(g) are repeated at least 500 times and wherein a SNP designated as a candidate SNP at least 200 times is identified as a SNP useful for analyzing genetic samples.

5. The method of claim 1, wherein the method is used to identify at least 10 SNPs useful for distinguishing genetic samples.

6. A method for identifying a panel of SNPs useful for analyzing a genetic sample, the method comprising:
   (a) using the method of claim 1 to identify a plurality of SNPs useful for analyzing a genetic sample;
   (b) excluding at least one of the plurality of SNPs; and
   (c) identifying the remaining SNPs as a panel of SNPs useful for analyzing a genetic sample.

7. The method of claim 6, wherein at least one SNP located in an intron is excluded.

8. The method of claim 6, wherein at least one SNP located in a region subject to loss of heterozygosity is excluded.

9. The method of claim 6, wherein at least one SNP having a heterozygosity rate that differs more than 2% between Caucasian and Asian populations is excluded.

10. The method of claim 6, wherein at least one SNP having a heterozygosity rate that differs more than 2% between Caucasian and African American populations is excluded.

11. The method of claim 6, wherein at least one SNP having a heterozygosity rate that differs more than 2% between Asian and African American populations is excluded.

12. A method for analyzing a genetic sample, the method comprising:
   (a) obtaining a first genetic sample;
   (b) analyzing the genotype of the genetic sample at each SNP in a set of SNPs identified as useful for analyzing genetic samples, wherein each SNP in the set of SNPs was identified using the method of claim 1; and
   (b) comparing the genotype of the genetic sample at each SNP in the set of SNPs to the genotype of a second genetic sample at each SNP in the set of SNPs to determine if the first and second genetic samples are the same or different.

* * * * *

UNITED STATES PATENT AND TRADEMARK OFFICE
CERTIFICATE OF CORRECTION

| | | |
|---|---|---|
| PATENT NO. | : 7,981,609 B2 | Page 1 of 1 |
| APPLICATION NO. | : 11/811149 | |
| DATED | : July 19, 2011 | |
| INVENTOR(S) | : Mark A. Rubin et al. | |

It is certified that error appears in the above-identified patent and that said Letters Patent is hereby corrected as shown below:

Title page, Column 2 (Other Publications), Line 2, delete "Hypertriglyceridaemic" and insert -- Hypertriglyceridemic --, Title page, Column 2 (Other Publications), Line 2, delete "Atheroscleorsis," and insert -- Atherosclerosis, --, Title page, Column 2 (Other Publications), Line 6, delete "mmortal" and insert -- immortal --, In Claim 12, delete "(b)" and insert -- (c) --

Signed and Sealed this
Twenty-second Day of November, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,981,609 B2 | |
| APPLICATION NO. | : 11/811149 | |
| DATED | : July 19, 2011 | |
| INVENTOR(S) | : Mark A. Rubin et al. | |

It is certified that error appears in the above-identified patent and that said Letters Patent is hereby corrected as shown below:

Title page, Column 2 (Other Publications), Line 2, delete "Hypertriglyceridaemic" and insert -- Hypertriglyceridemic --, Title page, Column 2 (Other Publications), Line 2, delete "Atheroscleorsis," and insert -- Atherosclerosis, --, Title page, Column 2 (Other Publications), Line 6, delete "mmortal" and insert -- immortal --, Column 50, line 42 (Claim 12, line 8) delete "(b)" and insert -- (c) --.

This certificate supersedes the Certificate of Correction issued November 22, 2011.

Signed and Sealed this
Third Day of January, 2012

David J. Kappos
*Director of the United States Patent and Trademark Office*